United States Patent [19]

Anderson et al.

[11] Patent Number: 5,550,213
[45] Date of Patent: Aug. 27, 1996

[54] INHIBITORS OF UROKINASE PLASMINOGEN ACTIVATOR

[75] Inventors: Stephen Anderson, Princeton; Raymond Ryan, Trenton, both of N.J.

[73] Assignee: Rutgers, The State University of New Jersey, Piscataway, N.J.

[21] Appl. No.: 173,102

[22] Filed: Dec. 27, 1993

[51] Int. Cl.$^6$ ............... C07K 14/00; C07K 14/465; A61K 38/00; A61K 38/57
[52] U.S. Cl. ............................................. 530/324; 530/300
[58] Field of Search ................. 514/2; 530/300; 435/190

[56] References Cited

U.S. PATENT DOCUMENTS

| | | | |
|---|---|---|---|
| 4,258,030 | 3/1981 | Sasaki et al. | 424/94 |
| 4,851,345 | 7/1989 | Hayashi et al. | 435/215 |
| 4,952,512 | 8/1990 | Lostukoff | 435/320 |
| 5,004,609 | 4/1991 | Hayashi et al. | 424/94.3 |
| 5,098,840 | 3/1992 | Kasai et al. | 435/215 |

FOREIGN PATENT DOCUMENTS

WO88/05081 7/1988 WIPO.

OTHER PUBLICATIONS

Fujinaga et al J. Mol. Biol. 195 pp. 397–418 (1987).
Turpeinen et al Biochem J. 254 pp. 911–914 (1980).
Schellenberger, V., et al., "Mapping the S' Subsites of Serine Proteases Using Acyl Transfer to Mixtures of Peptide Nucleophiles," *Biochemistry Soc.* 32: 4349–4353 (1993).
Hedstrom, L., et al., "Converting Trypsin to Chymotrypsin: The Role of Surface Loops," *Science* 255:1249–1253 (1992).
Laskowski, Jr., M., et al., "Design of Highly Specific Inhibitors of Serine Proteinases" *Abstract: Protein Recognition of Immobilized Ligands,* Alan R. Liss, Inc. pp. 149–168 (1989).
Madison, E. L. et al., "Serpin–Resistant Mutants of Human Tissue–Type Plasminogen Activator," *Nature* 339:721–724 (1989).
Blasi, F. et al., "Urokinase–Type Plasminogen Activator: Proenzyme, Receptor, and Inhibitors," *J. Cell. Biol.* 104:801–804 (1987).
Carrell, R. W. et al., "Mobile Reactive Centre of Serpins and the Control of Thrombosis," *Nature* 353:576–578 (1991).
Yu, H. et al., "Relationship between Secreted Urokinase Plasminogen Activator Activity and Metastatic Potential in Murine B16 Cells Transfected with Human Urokinase Sense and Antisense Genes," *Canc. Res.* 50:7623–7633 (1990).
Fujinaga, M. et al., "Crystal and Molecular Structures of the Complex of α–Chymotrypsin with its Inhibitor Turkey Ovomucoid Third Domain at 1.8 Å Resolution," *J. Molec. Biol.* 195:397 (1987).

*Primary Examiner*—Robert A. Wax
*Assistant Examiner*—William W. Moore
*Attorney, Agent, or Firm*—Howrey & Simon; Jeffrey T. Auerbach

[57] ABSTRACT

A low molecular weight, reversible, proteinaceous inhibitor specific for urokinase plasminogen activator is disclosed. Methods for designing, constructing and using this and other such specific inhibitors of urokinase plasminogen activator are also disclosed.

16 Claims, 5 Drawing Sheets

INHIBITORS OF UROKINASE PLASMINOGEN ACTIVATOR

FIELD OF THE INVENTION

The invention relates to the design, construction and use of a low molecular weight, reversible, proteinaceous inhibitor specific for urokinase plasminogen activator.

BACKGROUND OF THE INVENTION:

I. Plasminogen and Plasminogen Activators

The serum protein, plasminogen, plays an integral role in the proteolytic dissolution (or fibrinolysis) of blood clots. Plasminogen is an inactive "proenzyme." It has a specific affinity for fibrin, and thus becomes incorporated into blood clots as they form. Plasminogen's proteolytic activity is released by "plasminogen activators" ("PA") that specifically cleave the molecule to yield the active protease, plasmin. Plasmin is capable of digesting the fibrin threads of blood clots, as well as other substances involved in creating blood clots, such as fibrinogen, factor V, factor VIII, prothrombin, and factor XII (for review, see Danø, K. et al., *Adv. Canc. Res.* 44:139–266 (1985), herein incorporated by reference)).

Plasmin is a serine protease, and exhibits substantial amino acid and mechanistic homology with trypsin, chymotrypsin, and pancreatic elastase. Plasmin has a relatively broad trypsin-like specificity, hydrolyzing proteins and peptides at lysyl and arginyl bonds (Castellino, R. W. et al., *Meth. Enzymol.* 80:365–380 (1981); Dane, K. et al., *Adv. Canc. Res.* 44:139–266 (1985)).

Agents that are capable of activating plasminogen (i.e. converting it to plasmin) have been extensively studied. Two classes of natural mammalian plasminogen activators have been described: urokinase-type plasminogen activator and tissue-type plasminogen activator (Dane, K. et al., *Adv. Canc. Res.* 44:139–266 (1985); Devlin, et al., PCT appl. WO88/05081; Kasaia et al., U.S. Pat. No. 5,098,840; Hayashi, S. et al., U.S. Pat. No. 4,851,345; Sasaki et al., U.S. Pat. No. 4,258,030; Hayashi, S. et al., U.S. Pat. No. 5,004,609; Pyke, C. et al., *Amer. J. Pathol.* 138:1059–1067 (1991); Madison, E. L. et al., *Nature* 339:721–724 (1989); Blasi, F. et al., *J. Cell. Biol.* 104:801–804 (1987)). These two classes of molecules can be distinguished immunologically, by tissue localization, and by the stimulation of their activity by fibrin. In addition, a third plasminogen activator, streptokinase, has also been described. Streptokinase differs from urokinase and tPA in that it is a bacterial protein produced by the streptococci.

Urokinase-type plasminogen activator (UK) is a multi-domain protein with one domain being a trypsin-like serine protease (Castellino, R. W. et al., *Meth. Enzymol.* 80:365–380 (1981); Dane, K. et al., *Adv. Canc. Res.* 44:139–266 (1985); Straßburger, W. et al., *FEBS Lett.* 157:219–223 (1983)). This protease domain converts plasminogen to plasmin by cleavage at an arginyl residue (Castellino, R. W. et al., *Meth. Enzymol.* 80:365–380 (1981); Danø, K. et al., *Adv. Canc. Res.* 44:139–266 (1985)). The amino acid sequence and three-dimensional structure of several serine proteases, including trypsin, chymotrypsin, and elastase have been deduced (Danø, K. et al., *Adv. Canc. Res.* 44:139–266 (1985); Straßburger, W. et al., *FEBS Lett.* 157:219–223 (1983)).

Urokinase is synthesized in the kidneys, and can be recovered from urine. It is initially produced as a single chain protein, "pro-urokinase" that can be proteolytically cleaved by plasmin into an active two-chain protein (Devlin, et al., PCT appl. WO88/05081).

Tissue-type plasminogen activator (tPA) is produced by the cells that line the lumen of blood vessels or endothelial cells. Like urokinase, tPA is also initially produced as a single-chain molecule (Rijken, D. G. et al., *J. Biol. Chem.* 256:7035–7041 (1981); Pennica, D. et al., *Nature* 301:214–221 (1983)).

The known plasminogen activators differ significantly in characteristics such as their biological half-lives and their preference for fibrin. All three classes of activators have been widely used as thrombolytic agents for the treatment of thrombosis in myocardial infarction, stroke, arterial occlusion, etc. (Kasai et al., U.S. Pat. No. 5,098,840; Hayashi et al., U.S. Pat. No. 5,004,609; Hayashi et al., U.S. Pat. No. 4,851,345; Sasaki et al., U.S. Pat. No. 4,258,030).

II. Inhibitors of Plasminogen Activators

The regulation of fibrinolysis is crucial to the normal functioning of the circulatory system. Thus, the activity of serum proteases (such as urokinase or tPA) capable of activating plasminogen must be carefully regulated to ensure that clot formation and dissolution can occur. One manner in which such control is mediated concerns the regulated synthesis of inhibitors of plasminogen activators.

Three classes of naturally occurring physiological inhibitors of the plasminogen activators have been identified: the endothelial cell type PA-inhibitor (PAI-1), the placental type PA-inhibitor (PAI-2), and protease nexin-I (Sprengers, E. D. et al., *Blood* 69:381–387 (1987); Blasi, F. et al., *J. Cell Biol.* 104:801–804 (1987); Madison, E. L. et al., *Nature* 339:721–724 (1989); Carrell, R. W. et al., *Nature* 353:576–578 (1991); Lostukoff et al., U.S. Pat. No. 4,952,512; all herein incorporated by reference). Such inhibitors comprise nearly 10% of the total protein in blood plasma. They control a variety of critical events associated with connective tissue turnover, coagulation, fibrinolysis, complement activation and inflammatory reactions. Their function in the regulation of the fibrinolytic system has not yet been fully clarified.

PAI-1 and PAI-2 have an approximate molecular weight of 50,000. They differ in immunological reactivity and in their physiological characteristics (Blasi, F. et al., *J. Cell Biol.* 104:801–804 (1987)). Whereas these inhibitors are specific for PA, the protease nexin I inhibits plasmin, thrombin, and other trypsin-like serine proteases in addition to PA (Blasi, F. et al., *J. Cell Biol.* 104:801–804 (1987)).

PAI-1 is synthesized by a wide variety of cell types, including endothelial cells, hepatocytes, several hepatoma cell lines, granulosa cells, and possibly smooth muscle cells (Sprengers, E. D. et al., *Blood* 69:381–387 (1987); Blasi, F. et al., *J. Cell Biol.* 104:801–804 (1987)). PAI-1 interacts with both urokinase and tPA to form a stable bimolecular complex that inactivates both the inhibitor and the PA (Kruithof, C.K.O. et al., *Thromb.-Haemost.* 55:65–68 (1986)). PAI-2 was first identified in placental tissue. The inhibitor has been purified to homogeneity and found to have a molecular weight of 48,000. It is not generally present in serum samples (Sprengers, E. D. et al., *Blood* 69:381–387 (1987)). Protease nexin I is a 43,000 protein that exhibits a broad activity against trypsin-like serine proteases. It is synthesized by fibroblasts, heart muscle cells, and kidney epithelial cells (Sprengers, E. D. et al., *Blood* 69:381–387 (1987)).

III. The Role of Plasminogen Activators in Cancer

Metastasis involves the escape of a tumor cell from the tumor, its translation to a new site, and its successful invasion of the tissue of the new site and vascularization there to create a new tumor locus. The membranes of vascular or lymphatic vessels and dense connective tissue pose natural obstacles to the metastasis of tumor cells. The observation that explants of cancer tissue consistently caused proteolytic degradation eventually led to the recognition that tumor cells released a plasminogen activator capable of converting plasminogen to plasmin (see, for review, Danø, K. et al., *Adv. Canc. Res.* 44:139–266 (1985)). By secreting such a plasminogen activator, tumor cells are able to initiate a cascade of reactions that results in the localized proteolysis needed for tumor cell dissemination (Ossowski, L., *Cell* 52:321–328 (1988); Yu, H. et al., *Canc. Res.* 50:7623–7633 (1990)).

Urokinase has been found to be secreted by a variety of tumor types, including lung, colon and breast (see, Danø, K. et al., *Adv. Canc. Res.* 44:139–266 (1985) for review). Urokinase has been found to have an important role in the metastasis of tumor cells (Yu, H. et al., *Canc. Res.* 50:7623–7633 (1990); Ossowski, L., *Cell* 52:321–328 (1988); Ossoswki, L. et al., *Canc. Res.* 51:274–281 (1991)). A positive correlation has been reported between the metastatic potential of tumor cells and their capacity to produce urokinase (Axelrod, J. H. et al., *Molec. Cell. Biol.* 9:2133–2141 (1989); Yu, H. et al., *Canc. Res.* 50:7623–7633 (1990)).

Significantly, urokinase appears to mediate its effect at the initial stage of metastasis by facilitating the escape of tumor cells from the primary tumor site. Indeed, inhibitors of urokinase, tested in a metastatic mouse model, were ineffective in preventing either the translation or invasion of of metastatic cells that had been injected into the animal's bloodstream (Ostrowski, L. E. et al., *Canc. Res.* 46:4121–4128 (1986)). Thus, UK inhibitors would be an especially desirable inhibitor of tumor metastasis because they would not allow even the first stage of metastasis to occur (i.e. escape of cells from the primary tumor site).

As indicated, urokinase is also produced in response to many natural physiological conditions. The implantation of a fertilized egg into the uterine wall provides an example of localized proteolysis, mediated by urokinase, that occurs in normal tissue (Dane, K. et al., *Adv. Canc. Res.* 44:139–266 (1985)).

In view of the role of plasminogen activators, in general, and of urokinase, in particular, in the metastasis of tumor cells, and in mediating uterine implantation, it would be desirable to have a low molecular weight, reversible, proteinaceous inhibitor specific for urokinase that could be employed in the treatment of metastatic cancers, or in the prevention of pregnancy. No low molecular weight, protein inhibitors with significant functional affinity for UK have been previously identified. The present invention provides such molecules, and methods for their use.

SUMMARY OF THE INVENTION

Urokinase plasminogen activator (UK) is a multi-domain protein with one domain being a serine protease showing sequence homology to the trypsin family of serine proteases. This protease domain converts plasminogen to plasmin. The present invention relates to the design, construction, and use of low molecular weight, reversible, proteinaceous inhibitors specific for urokinase plasminogen activator.

In detail, the invention provides a low molecular weight proteinaceous inhibitor of urokinase, and, in particular, a Kazal-type inhibitor of urokinase. The invention particularly provides Kazal-type inhibitors of urokinase that are related to human pancreatic secretory trypsin inhibitor and/or an avian ovomucoid third domain.

The invention further provides Kazal-type inhibitors of urokinase that have mutations in residues of an avian ovomucoid third domain.

The invention further provides a low molecular weight inhibitor of urokinase that is joined to another moiety, such as an antibody, a ligand for a receptor molecule, or a receptor molecule.

In particular, the invention provides low molecular weight proteinaceous inhibitors of urokinase having the amino acid sequence:

Val—Asp—Cys—Ser—Glu—Tyr—Pro—Lys—Pro—Ala—
Cys—Gly—Arg—Thr—Gly—His—Pro—Leu—Cys—Gly—
Ser—Asp—Asn—Lys—Thr—Tyr—Gly—Asn—Lys—Cys—
Asn—Phe—Cys—Asn—Ala—Val—Val—Glu—Ser—Asn—
Gly—Thr—Leu—Thr—Leu—Ser—His—Phe—Gly—Lys—
Cys;
or
Val—Asp—Cys—Ser—Glu—Tyr—Pro—Lys—Pro—Ala—
Cys—Ala—Arg—Met—Ala—Ala—Pro—Leu—Cys—Gly—
Ser—Asp—Asn—Lys—Thr—Tyr—Gly—Asn—Lys—Cys—
Asn—Phe—Cys—Asn—Ala—Val—Val—Glu—Ser—Asn—
Gly—Thr—Leu—Thr—Leu—Ser—His—Phe—Gly—Lys—
Cys;
or
Val—Asp—Cys—Ser—Glu—Tyr—Pro—Lys—Pro—Ala—
Cys—Gly—Arg—Val—Val—Gly—Pro—Leu—Cys—Gly—
Ser—Asp—Asn—Lys—Thr—Tyr—Gly—Asn—Lys—Cys—
Asn—Phe—Cys—Asn—Ala—Val—Val—Glu—Ser—Asn—
Gly—Thr—Leu—Thr—Leu—Ser—His—Phe—Gly—Lys—
Cys;
or
Val—Asp—Cys—Ser—Glu—Tyr—Pro—Lys—Pro—Ala—
Cys—Ala—Arg—Ser—Ser—Ala—Pro—Leu—Cys—Gly—
Ser—Asp—Asn—Lys—Thr—Tyr—Gly—Asn—Lys—Cys—
Asn—Phe—Cys—Asn—Ala—Val—Val—Glu—Ser—Asn—
Gly—Thr—Leu—Thr—Leu—Ser—His—Phe—Gly—Lys—
Cys.

The invention also provides a DNA molecule that encodes a low molecular weight proteinaceous inhibitor of urokinase, and more specifically each of the above recited inhibitors.

The invention also provides a method of preventing or attenuating a urokinase-dependent process (such as the metastasis of a tumor, ovulation, uterine implantation of a fertilized ova, etc.) in an individual which comprises administering to the individual an effective amount of a low molecular weight proteinaceous inhibitor of urokinase.

The invention also provides an antineoplastic agent comprising a low molecular weight proteinaceous inhibitor of urokinase.

The invention further provides a contraceptive agent comprising a low molecular weight proteinaceous inhibitor of urokinase.

Figure 1:
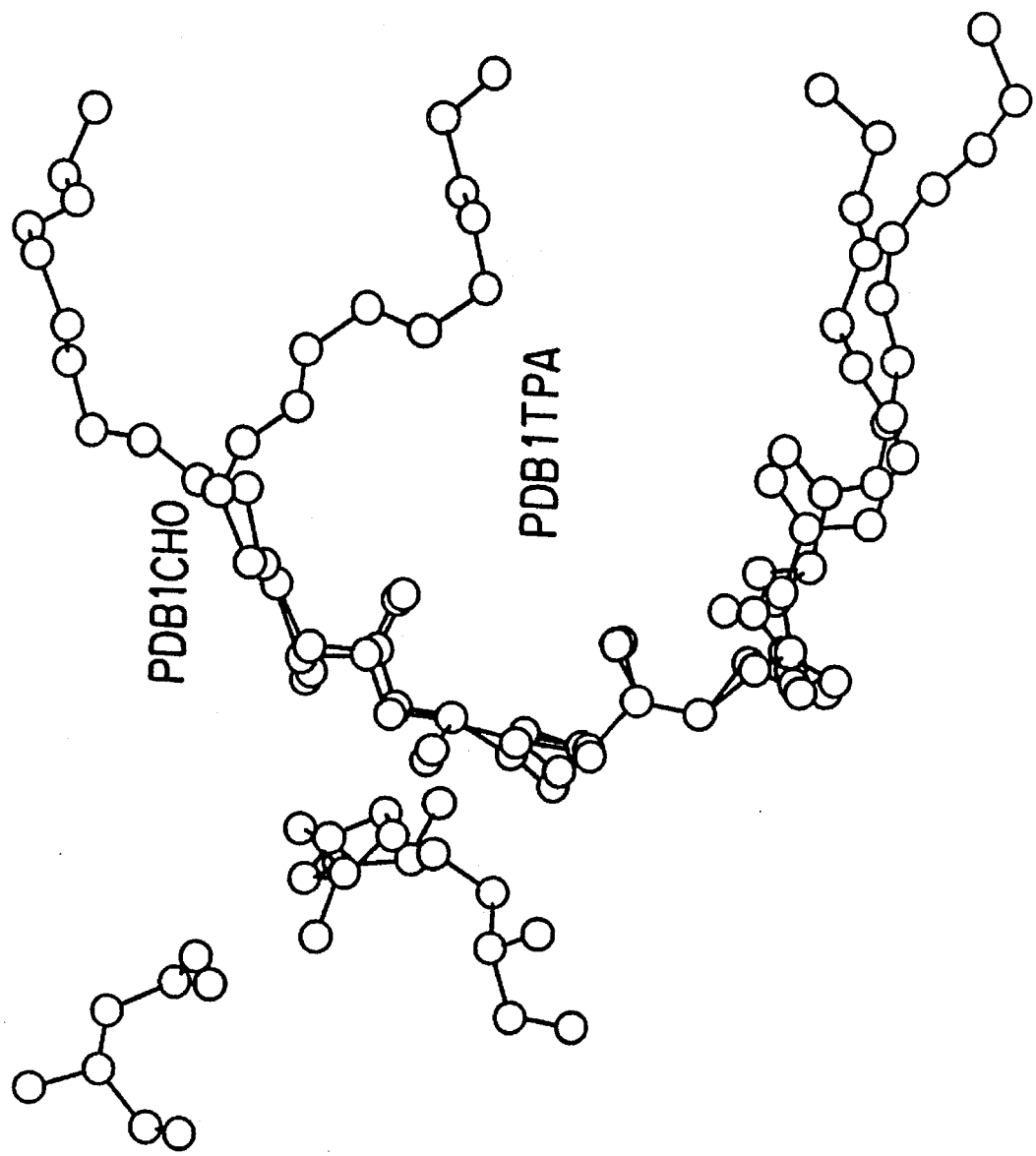
FIG. 1 is an illustration of the canonical loop by a superimposition of the backbone nitrogen, α-carbons, carbonyl carbons, and side chain β-carbons, with an RMS deviation of 0.2 Å. The OM3TKY (labelled PDB1CHO), and BPTI (labelled PDB1TPA), from residue P6 to residue P6' are shown. The catalytic triad in relation to the P1 loop is also shown.

DESCRIPTION OF THE PREFERRED EMBODIMENTS:

The present invention concerns the design, construction, and use of low molecular weight, reversible, proteinaceous inhibitors specific for urokinase plasminogen activator. To accomplish this goal, the present invention exploits homologies and similarities in structure between urokinase and the trypsin-like serine proteases to model the serine protease domain of UK. Such inhibitors can be designed by computer-assisted modeling based upon the structure of urokinase, and its similarity to other proteins.

Increasingly, the correlation between the structures of known proteins and the sequence of a target protein is made using computer simulations (van Gunsteren, V. F., *Prot. Engin.* 2:5–13 (1988); Yang, M. M. et al., In: *Reaction Centers of Photosynthetic Bacteria*, (Michel-Beyerle, Ed.), Springer-Verlag, Germany (1990), pp 209–218), databases (Moult, J. et al., *Proteins* 1:146–163 (1987); Klein, P. et al., *Biopolymers* 25:1659–1672 (1986); Nakashima, H. et al., *J. Biochem. (Tokyo)* 99:153–162 ((1986); Deleage, G. et al., *Prot. Engin.* 1:289–294 (1987)); neural networks (Qian, N. et al., *J. Molec. Biol.* 202:865–884 (1988); Holley, L. H. et al., *Proc. Natl. Acad. Sci. (U.S.A.)* 86:152–156 (1989); Bohr, H. et al., *FEBS Lett.* 241:223–228 (1988)); or expert systems (Robson, B. et al., *J. Molec. Graphics* 5:8–17 (1987)). See, generally, Fasman, G. R., *TIBS* 14:295–299 (1989)).

The use of computers or computer-assisted methods in analyzing the structure of proteins is discussed, for example, in U.S. Pat. Nos. 4,704,692 (Ladner); 4,760,025 (Estell et al.); 4,853,871 (Pantoliano et al.); and 4,908,773 (Pantoliano et al.).

Modeling information obtained for urokinase can be employed to define inhibitors of tPA as well as for urokinase. UK and tPA are both multi-domain proteins. Both have a serine protease domain and an EGF-like domain. UK has one kringle domain, while t-PA has two such domains, as well as a fibronectin-like finger domain (Danø, K. et al., *Adv. Canc. Res.* 44:139–266 (1985)). Both plasminogen activators cleave the same substrate, plasminogen, at the same arginyl site, Arg 561 in plasminogen (Castellino, R. W. et al., *Meth. Enzymol.* 80:365–380 (1981)). Both plasminogen activators have the same natural inhibitors (Sprengers, E. D. et al., *Blood* 69:381–387 (1987)). The functional distinction between the two plasminogen activators derives in part from the localization of the two enzymes within an organism. This localization is a function of the non-proteolytic domains (Behrendt, N. et al., *J. Biol. Chem.* 266:7842–7847 (1991); Blasi, F. et al., *J. Cell Biol.* 104:801–804 (1987); Danø, K. et al., *Adv. Canc. Res.* 44:139–266 (1985)). Also, the naturally occurring inhibitors to the plasminogen activators are preferential in reactivity to UK or tPA, but not solely specific for either one (Sprengers, E. D. et al., *Blood* 69:381–387 (1987)). Using UK as a model system for comparison with tPA allows for a finer determination of what governs recognition and specificity in the protease domains.

I. Trypsin-Like Serine Proteases

The trypsin-like serine proteases are hydrolases which utilize a catalytic triad of amino acids made up of histidine, serine, and aspartic acid to cleave a peptide substrate at the peptide bond between two residues of the substrate, S1 and S1'. The nomenclature for the substrate residues derives from their position relative to the scissile (S) peptide bond (Wynn, R., Ph.D. Dissertation, Purdue University, pp 28–30; 50–115 (1990)). This numbering extends outward in either direction from the scissile bond, which is the site of cleavage. Enzymology and kinetics studies, coupled with crystallographically determined models of serine proteases, have enabled researchers to describe in molecular detail the mechanism of serine-protease catalysis (Wynn, R., Ph.D. Dissertation, Purdue University, pp 28–30; 50–115 (1990)). The three-dimensional structures of several trypsin-like serine proteases show that the structural homology of this enzyme family extends beyond primary structure to the three-dimensional structures (Fujinaga, M. et al., *J. Molec. Biol.* 195:397 (1987); Huber, R. et al., *J. Molec. Biol.* 89:73 (1974); Straβburger, W. et al., *FEBS Lett.* 157:219–223 (1983)). These structural similarities have helped to emphasize the structural and functional relationships of the catalytic mechanism, but the details of the specificity mechanisms of these proteases are still unclear.

The differences among the homologous protease structures have also been used to understand the functional differences in substrate specificity between many members of the trypsin-like serine protease family. While the mechanism of proteolysis is the same for these enzymes, the specificity of the enzymes is quite varied (Table 1).

TABLE 1

| TRYPSIN-LIKE SERINE PROTEASES | |
|---|---|
| Protease | S1 Specificity |
| Trypsin | Arg, Lys |
| Chymotrypsin | Phe, Tyr, Trp |
| Elastase | Leu, Val, Ala |
| Thrombin | Arg, Lys |
| Plasminogen | Arg, Lys |
| tPA, UK | Arg, Lys |

The cleavage specificity of a trypsin-like serine protease is thought to rely primarily on residues in the active site pocket, which interact with the S1 residue of the substrate (Chase, T. et al., *Biochem. Biophys. Res. Commun.* 29:508–514 (1967); Hedstrom, L. et al., *Science* 255:1249–1253 (1992); Wynn, R., Ph.D. Dissertation, Purdue University, pp 28–30; 50–115 (1990)). The S1 specificity for basic residues has been attributed to a complementary charge of an aspartic acid at position 189 (trypsin/chymotrypsin numbering) (Hedstrom, L. et al., *Science* 255:1249–1253 (1992)), which lies at the bottom of the protease active site. More recent studies have indicated that loops of the protease outside the active site pocket help determine the substrate specificity (Hedstrom, L. et al., *Science* 255:1249–1253 (1992)).

II. Proteinaceous Serine Protease Inhibitors

A structural understanding of the specificity of the trypsin-like proteases can be achieved through chemical and crystallographic studies of various enzymes in complex with protease inhibitors, synthetic and proteinaceous. As indicated in Table 2, there are many families of proteinaceous serine protease inhibitors (Onesti, S. et al., *J. Molec. Biol.* 217:153–176 (1991); Wynn, R., Ph.D. Dissertation, Purdue University, pp 28–30; 50–115 (1990)).

TABLE 2

| PROTEIN SERINE PROTEASE INHIBITORS | | |
|---|---|---|
| Animals | Plants | Microbial |
| Kunitz (e.g., BPTI) | Soybean Trypsin (Kunitz) | SSI |
| Kazal (e.g., PSTI) | Soybean (Bowman-Birk) | |
| Ascaris | Potato 1 | |
| Hirudin | Barley Trypsin | |
| Serpin | Squash | |

Most of the above-listed inhibitors act reversibly. The serpin (SERine Protease INhibitor) family of inhibitors, however, act irreversibly (Carrell, R. W. et al., *Nature* 353:576–578 (1991); Sprengers, E. D. et al., *Blood* 69:381–387 (1987)). Urokinase's two known native inhibitors, PAI-1 and PAI-2 (Sprengers, E. D. et al., *Blood* 69:381–387 (1987)) are members of the serpin family of inhibitors (Christensen, U. et al., Thromb.-Haemost. 48:24–26 (1982); Kruithof, C.K.O. et al., Thromb.-Haemost. 55:65–68 (1986); Sprengers, E. D. et al., *Blood* 69:381–387 (1987)). The structure of these serpin inhibitors when complexed with a protease is not known. Another serpin, protease nexin-1, has also been seen to have some inhibitory effect against UK, though not against tPA (Sprengers, E. D. et al., *Blood* 69:381–387 (1987)).

The sizes of these proteinaceous inhibitors vary greatly, ranging from approximately 5 kD for the squash inhibitor to about 60 kD for the serpins. The nomenclature for the residues of the inhibitors mimics that for protease substrates, using the labels P1 and P1' in place of S1 and S1' (Wynn, R., Ph.D. Dissertation, Purdue University, pp 28–30; 50–115 (1990)).

The crystal and NMR structures of several inhibitor-protease complexes have been determined (Bode, W. et al., *Eur. J. biochem.* 147:387–395 (1985); Fujinaga, M. et al., *J. Molec. Biol.* 195:397 (1987); Huber, R. et al., *J. Molec. Biol.* 89:73 (1974); Papamokos, E. et al., *J. Molec. Biol.* 158:515–537 (1982)).

An interesting feature common to these complexed structures is the canonical active site loop structure of the inhibitor (Bode, W. et al., *Eur. J. biochem.* 147:387–395 (1985); Carrell, R. W. et al., *Nature* 353:576–578 (1991); Onesti, S. et al., *J. Molec. Biol.* 217:153–176 (1991); Wynn, R., Ph.D. Dissertation, Purdue University, pp 28–30; 50–115 (1990)). This canonical loop is the inhibitor loop that binds the protease active site pocket; P1 and P1' appear the same distance apart as they do in the non-complexed inhibitor. Conformational similarity of the P1 loop between quite different inhibitors, particularly in the backbone conformation, has been remarked upon (Bode, W. et al., *Eur. J. biochem.* 147:387–395 (1985); Onesti, S. et al., *J. Molec. Biol.* 217:153–176 (1991); Wynn, R., Ph.D. Dissertation, Purdue University, pp 28–30; 50–115 (1990)).

The serpins are, however, an exception to these observations. No crystal structures have been determined for inhibitory serpins in either their native (uncleaved) state, or in complex with a protease. Those crystal structures that do exist are of either the non-inhibitory serpin-like protein, ovalbumin, or they are of the stable form of inhibitory serpins, cleaved at the P1-P1' peptide bond (Carrell, R. W. et al., *Nature* 353:576–578 (1991); Stein, P. E. et al., *Nature* 347:99–102 (1990)). The serpin structures do not exhibit the canonical inhibitor loop seen in other inhibitor-protease complexes. The non-inhibitory ovalbumin has an alpha helix corresponding to the active site loop (Stein, P. E. et al., *Nature* 347:99–102 (1990)), and in the structures of the cleaved inhibitory serpins, the P1 and P1' residues are almost 70A apart from each other (Carrell, R. W. et al., *Nature* 353:576–578 (1991)).

III. Production of Urokinase Inhibitors

A. Identification of Urokinase Inhibitors

Due to the lack of structural knowledge of serpins complexed with proteases, the small, protein protease inhibitors were used as a model system for protein recognition.

In the initial step in the modelling, the amino acid sequences of urokinase (UK), tissue plasminogen activator (tPA), bovine chymotrypsinogen (CHYM), bovine trypsin (TRYP) and porcine elastase (ELASTASE) serine protease domains were aligned. For this purpose, the protein sequence alignment of these proteins determined by Straßburger, W. et al., *FEBS Lett.* 157:219–223 (1983), herein incorporated by reference, was used.

The UK active site and surrounding structure of UK was modelled using a structure of trypsin complexed with bovine pancreatic trypsin inhibitor, BPTI (Brookhaven file 1TPA (Huber, R. et al., *J. Molec. Biol.* 89:73 (1974)) as a starting framework. The modelling was done using Insight, Version 2.5 (Biosym), although other suitable programs or methods could also have been employed. For such modeling, a series of amino acid substitutions were made in the trypsin structure so as to introduce the corresponding residues present in UK. To simplify the modeling of UK, the enzymes' surface residues closest to the active site pocket, judged as being important for a working model, were preferentially replaced.

In order to maximize the alignment of the amino acid sequences of trypsin and urokinase, three "loops" are preferably created in the urokinase sequence to account for the presence of amino acid residues in urokinase that lack a counterpart in trypsin (i.e. possess a "gap" when properly aligned). Thus, in order to adapt the structure of trypsin to form a model for urokinase, it was desirable to add a series of three insertions at the "loop" points in the trypsin structure.

The present invention follows the convention of Straßburger, W. et al. (*FEBS Lett.* 157:219–223 (1983)) in referring to the residues of the aligned molecules with reference to the corresponding residue number of chymotrypsinogen. Thus for example, residue 35 of trypsin is that residue of trypsin which corresponds in location to residue 35 of chymotrypsinogen when the two molecules are aligned to maximize homology.

The first insertion was intended to "fill" the "gap" at residues 35 through 38 of trypsin. Residues 28–42 of elastase (Brookhaven files 1EST (Sawyer, L. et al,, *J. Molec. Biol.* 118:137 (1978))) were selected to comprise the first loop insertion. Thus, these residues replaced the region of trypsin in the model that corresponded in alignment to chymotrypsinogen residues 28–42. The one amino acid corresponding to urokinase that was still lacking (i.e. His 36) was inserted singly into the break between residues 34 and 35 of elastase.

The second insertion was based on a loop originally derived from the Brookhaven file 1CAC, and selected by an internal geometry search of the Protein Database. Backbone torsion angles were checked by the Ramachandran function of TOM (FRODO for the IRIS SG). Amino acid substitutions were made in these insertions to obtain UK sequences.

The third insertion was also taken from elastase, and covered the "gap" between residues 99 and 100 of trypsin. This insertion actually replaced trypsin residues from 90 to 105 with the corresponding residues in elastase.

Other gaps in the alignment of trypsin and urokinase were deemed to be sufficiently far from the inhibitor binding determinants as to not play a vital role in the protease-inhibitor interaction. Accordingly, they were not "corrected" in the model.

In order to identify a suitable small inhibitor of urokinase, the complexed structures of known proteases and their inhibitors were considered. Among such protease inhibitors whose protease complex structures are known are Bovine Pancreatic Trypsin Inhibitor (BPTI), a Kunitz inhibitor (Huber, R. et al., *J. Molec. Biol.* 89:73 (1974); Wynn, R., Ph.D. Dissertation, Purdue University, pp 28–30; 50–115 (1990)), and some Avian Ovomucoid Third Domain (OM3) variants, which are Kazal-type inhibitors (Fujinaga, M. et al., *J. Molec. Biol.* 195:397 (1987); Papamokos, E. et al., *J. Molec. Biol.* 158:515–537 (1982), herein incorporated by reference). A third variety of proteinaceous protease inhibitors, from the soybean *E. latissima*, may also be used to design an inhibitor for plasminogen activator (Onesti, S. et al., *J. Molec. Biol.* 217:153–176 (1991)). Preferably, the desired inhibitor of urokinase is designed by modifying small protease inhibitors of well known structure, and most preferably, inhibitors from the Kazal-type family.

The modeling program was therefore used to complex BPTI with the protease "loops" surrounding the UK active site, thereby forming a UK-BPTI. Such complexing did not necessarily sterically interfere with a small inhibitor's placement in the active site pocket in this preliminary model. Likewise, no overtly poor charge interactions resulted from having BPTI in complex with the UK model. A "worst case" UK-BPTI model still only allowed for four poor steric interactions of the inhibitor and protease. These possible bad contacts were in region 37–42 of BPTI.

The UK-BPTI model was then compared with the structural model of chymotrypsin complexed with a second protease inhibitor, the ovomucoid third domain (OM3). A superimposition of the trypsin and chymotrypsin structures, using homologous amino acids in the proteases, gave a low RMS deviation for both the protease amino acids and the P1 loops of each inhibitor, residues P3 to P3'. A second superimposition of the two structures was performed using the alpha and beta carbons of P2 to P3' of each inhibitor, and the protease catalytic triad. Even though the side chains of each inhibitor were different from each other, the RMS deviation of backbone and beta carbon configuration of the inhibitors was below 0.2 A deviations (FIG. 1). FIG. 1 illustrates the canonical loop.

The interactions that the two inhibitors, BPTI and OM3 might have with the protease were evaluated using computer modeling. The BPTI P1 loop, though narrower from P4-P3', was found to be less extended in comparison with the P1 loop of OM3, and thus more discontinuous strands of BPTI could possibly interact with the protease model.

Kazal-type inhibitors display a great deal of flexibility in the P1 loop binding the protease active site, as evidenced by their ability to bind both trypsin-like and subtilisin-like proteases with different P1 loop conformations. BPTI is not known to have inhibitory effects against subtilases. These factors suggested that changes within the ovomucoid third domain (OM3) active site would cause fewer perturbations on the surrounding inhibitor structure than would changes in BPTI. Moreover, fewer mutations would be needed in order to make an OM3-derived inhibitor with affinity for UK.

Thus, the above-described computer modelling indicated that a desired UK inhibitor could be obtained via mutation of a Kazal-type inhibitor, and specifically the turkey ovomucoid third domain (OM3TKY) Kazal-type inhibitor.

By starting from OM3TKY, it was also possible to apply the results of many structural and functional studies that have been done to investigate amino acid substitutions within the OM3 framework (Empie, M. W. et al., *Biochem.* 21:2274–2284 (1982); Laskowski, M. et al., *Biochem.* 30:10832–10838 (1991); Papamokos, E. et al., *J. Molec. Biol.* 158:515–537 (1982); Wynn, R., Ph.D. Dissertation, Purdue University, pp 28–30; 50–115 (1990), all herein incorporated by reference). Laskowski and co-workers have mapped and summarized a list of primary and secondary contact sites of the OM3 domain variants against a spectrum of trypsin-like proteases. The consensus contact residues of OM3 domains is summarized in Table 3 (Laskowski, M. et al., *Biochem.* 30:10832–10838 (1991); Wynn, R., Ph.D. Dissertation, Purdue University, pp 28–30; 50–115 (1990)). In Table 3, primary contacts (1°) are defined by non-hydrogen atoms of the inhibitor that are within 4 A of non-hydrogen atoms of the protease. An asterisk (*) denotes a hydrogen bond interaction, while the dagger (†) denotes a residue participating in an ion-binding pair.

TABLE 3

PROTEASE CONTACT RESIDUES OF OM3

| Residue | 1° or 2° Contact | Main Chain (MC) or Side Chain (SC) Contact | Structurally Conserved |
|---|---|---|---|
| P6 | 1° | MC* | N |
| P5 | — | — | Y (Pro) |
| P4 | 1° | SC | N |
| P3 | — | — | Y (Cys) |
| P2 | 1° | SC* | N |
| P1 | 1° | SC, MC | N |
| P1' | 1° | SC | N |
| P2' | 1° | SC† | N |
| P3' | 1° | — | N |
| P14' | 2° | — | Y (Gly) |
| P15' | 2° | SC* | Y (Asn) |
| P18' | 1° | SC | N |

Those residues listed in Table 3 as structurally conserved are deemed important to maintain the inhibitors' structures, and not for value of their direct interaction with a protease (Wynn, R., Ph.D. Dissertation, Purdue University, pp 28–30; 50–115 (1990)). Primary contacts (1°) designate residues in the inhibitor P1 loop, or those residues which make direct contact with the protease. Secondary contacts (2°) are those residues of the inhibitor which interact indirectly via contacts with the P1 loop. Residue P14' seems to be conserved as a glycine in most OM3 domains, but whether the affects of substitutions at this site are intra-structural for the inhibitor, or contact determined between protease and inhibitor, is unclear. Effects on free energy and disassociation constants by substitutions at P14' have been shown to be non-additive (Wynn, R., Ph.D. Dissertation, Purdue University, pp 28–30; 50–115 (1990)).

Although changes in conserved structural residues, such as P5, P3, and P14' might yield strong inhibitors, such an alteration would potentially obscure the structural basis for any observed change in inhibitor specificity. Moreover, changes in any of the conserved structural residues might alter the inhibitor structure non-predictably. For these reasons, no changes were made at any conserved residues.

It is desirable to take advantage of the structurally conserved nature of the P1 loop. Since the backbone and carbon structures remain relatively constant, the nature of the side chains, whether basic, acidic, aliphatic, aromatic, long, or short, is a major determining factor for inhibitor affinity.

The knowledge of specificity determinants between tPA and PAI-1 (Madison, E. L. et al., Nature 339:721–724 (1989)) was an additional consideration in designing the desired inhibitor. tPA contains a loop corresponding to the first insertion (discussed above) in the UK model. This loop governs the interaction of tPA with PAI-1. This loop is located nearer the C-terminal P' residues of postulated inhibitor interactions, rather than on the N-terminal side of P1. The working model of UK in complex with inhibitors did not show any interaction with this loop. Likewise, changes in this loop did not seem to affect tPA activity against plasminogen, suggesting a specificity determinant further from the P1 loop.

Because it was desired that the inhibitors identified by the present invention would not simply have high affinity for UK, but would also have higher specificity for UK, the effect of changes in residues in the P1 loop was considered as a means to achieve more than arginyl specificity from P1. Specifically, changes were made in the P1 loop C-terminal to P1, in the P1'–P3' region nearest the t-PA loop. The region N-terminal to P2 was not altered, due to the presence of more structurally conserved residues in this part of the P1 loop.

As a result of the above modeling considerations, replacement of the short P1 loop of the OM3TKY with the region immediately surrounding the scissile bond of PAI-1, PAI-2, plasminogen, and Nexin-1 was considered a likely means for obtaining a urokinase-specific inhibitor. Table 4 shows the mutations identified as having potential for producing such an inhibitor.

The substituted residues are indicated with asterisks. The P1 residue, leucine, of OM3TKY is also indicated with an asterisk. The cysteines are in boldface, to indicate that they participate in disulfide bonds.

Other changes that could introduce greater loop flexibility are the introduction of glycine and serine residues in the P1'–P3' residues of the mutants. All of the potential mutants are bounded at P4' by the proline which induces a turn in the loop back into the cystine scaffold of the Kazal inhibitor. A Pro to Gly change at P4' has the potential to further increase P1 loop flexibility.

C. Possible Effects of Secondary Contacts

The mutations formed by replacement of OM3TKY active residues by the serpin and plasminogen residues leave a pocket between Asn 33 of OM3TKY and the position formerly occupied by Glu 19 (P1' of OM3TKY) (Wynn, R., Ph.D. Dissertation, Purdue University, pp 28–30; 50–115 (1990)). Asn 33 of OM3TKY is the P15' residue. This pocket, roughly the size of a methyl group might cause a slight collapse of the surrounding P1 backbone conformation, especially due to the glycines and alanines substituted at P2. The P15' Asn site has been seen as an important mediator of inhibitor affinity in other studies with avian ovomucoid third domains (Empie, M. W. et al., Biochem. 21:2274–2284 (1982); Laskowski, M. et al., Biochem. 30:10832–10838 (1991); Papamokos, E. et al., J. Molec. Biol. 158:515–537 (1982); Wynn, R., Ph.D. Dissertation, Purdue University, pp 28–30; 50–115 (1990)).

If one desired to prevent this pocket from permitting such a collapse to occur, the P15' in OM3TKY could be changed to one of the following three residues: glutamine, leucine, or isoleucine, in that order of preference.

In sum, the present invention uses a computer-assisted modeling method to identify inhibitors of urokinase and other proteins of similar structure.

D. Synthesis of Inhibitor Molecules

TABLE 4

MUTATIONS IN OM3TKY IDENTIFIED AS RESULTING IN A POTENTIAL UROKINASE INHIBITOR

| | | PROTEASE INHIBITOR | | | |
|---|---|---|---|---|---|
| RESIDUE | OM3TKY | Plasminogen Derived | PAI-2 Derived | PAI-1 Derived | Nexin Derived |
| P5 | P | P | P | P | P |
| P4 | A | A | A | A | A |
| P3 | C | C | C | C | C |
| P2 | T | G* | G* | A* | A* |
| P1 | L* | R* | R* | R* | R* |
| P1' | E | V* | T* | M* | S* |
| P2' | Y | V* | G* | A* | S* |
| P3' | R | G* | H* | A* | A* |
| P4' | P | P | P | P | P |
| P5' | L | L | L | L | L |
| P6' | C | C | C | C | C |
| P7' | G | G | G | G | G |
| P8' | S | S | S | S | S |
| P9' | D | D | D | D | D |

B. Structural Considerations in the P1 Loop All of the proteins with natural affinity for UK have a glycine or alanine at P2, as do all of the proposed mutants. The presence of a glycine or alanine would allow a greater deal of X-Ψ torsional freedom than the β-branched threonine of WT OM3TKY. Additionally, the Oγ of the P2 Thr in OM3TKY is known to hydrogen bond with the P1' residue backbone ((Wynn, R., Ph.D. Dissertation, Purdue University, pp 28–30; 50–115 (1990)), possibly conferring more rigidity on the P1 loop. The removal of this rigidity could also increase the flexibility of the loop in possible mutants.

The inhibitor molecules of the present invention may be made by chemical synthesis, such as by peptide synthesis. More preferably, the inhibitor molecules will be made using recombinant DNA technology. In this embodiment, gene sequences capable of expressing the inhibitor, or a fusion protein of the inhibitor with another protein, peptide or amino acid leader or trailing sequence, will be introduced into a vector, such as a cosmid, bacteriophage or plasmid and introduced into a suitable host cell.

Any means known in the art may be used to synthesize the oligonucleotides that encode the inhibitors of the present invention (Zamechik et al., *Proc. Natl. Acad. Sci. (U.S.A.)* 83:4143 (1986); Goodchild et al., *Proc. Natl. Acad. Sci. (U.S.A.).* 85:5507 (1988); Wickstrom et al., *Proc. Natl. Acad. Sci. (U.S.A.)* 85:1028; Holt, J. T. et al., *Mol. Cell. Biol.* 8:963 (1988); Gerwirtz, A. M. et al., *Science* 242:1303 (1988); Anfossi, G., et al., *Proc. Natl. Acad. Sci. (U.S.A.)* 86:3379 (1989); Becker, D., et al., EMBO J. 8:3679 (1989); all of which references are incorporated herein by reference) . Automated nucleic acid synthesizers may be employed for this purpose. In addition, desired nucleotides of any sequence can be obtained from any commercial supplier of such custom molecules.

Most preferably, such oligonucleotides may be prepared using solid phase "phosphoramidite synthesis." The synthesis is performed with the growing nucleotide chain attached to a solid support derivatized with the nucleotide which will be the 3'-hydroxyl end of the transcript or oligonucleotide. The method involves the cyclical synthesis of DNA using monomer units whose 5'-hydroxyl group is blocked (preferably with a 5'-DMT (dimethoxytrityl) group), and whose amino groups are blocked with either a benzoyl group (for the amino groups of cytosine and adenosine) or an isobutyryl group (to protect guanosine). Methods for producing such derivatives are well known in the art.

The DNA molecules thereby produced may be incorporated into "vector" molecules. The term "vector," as used herein is intended to denote any viral or plasmid molecule that is capable of being introduced (as by transformation, electroporation, transfection, etc.) and/or propagated (i.e. replicated) in a prokaryotic or eukaryotic cell. Suitable prokaryotic or eukaryotic vectors, as well as the methods for using them are disclosed, for example, by Sambrook, J. et al., In: *Molecular Cloning A Laboratory Manual,* 2nd Edition, (Cold Spring Harbor Laboratory Press, Cold Spring Harbor, N.Y. (1989), herein incorporated by reference).

For some purposes, such as the isolation of inhibitor in quantities sufficient to facilitate in vitro purification, it may be desirable to express the inhibitors of the present invention in prokaryotic hosts, especially bacteria using prokaryotic vectors. Preferred prokaryotic vectors include plasmids such as those capable of replication in *E. coli* such as, for example, pBR322, pEZZ318, ColE1, pSC101, pACYC 184, πVX. Such plasmids are, for example, disclosed by Sambrook, J. et al. (In: *Molecular Cloning, A Laboratory Manual,* 2nd Ed., Cold Spring Harbor Press, Cold Spring Harbor, N.Y. ( 1989 ) ) .

A preferred prokaryotic vector is one that mediates the expression of the protein as a fusion protein with staphylococcal protein A ("SPA"). Examples of such vectors include the pRIT 20 and pRIT 30 series of vectors (Nilsson, B. et al. (*Meth. Enzymol.* 185:144–161 (1990)). Because SpA fusions are expressed in diverse bacterial hosts, and direct the fusion protein into either the periplasmic space or the culture medium, such fusions facilitate the purification of the protein. Moreover, since SpA binds to the Fc portion of IgG, the fusion protein can be readily purified by immunoaffinity methods. The construction and use of such SpA fusion vectors is described by Nilsson, B. et al. (*Meth. Enzymol.* 185:144–161 (1990)), herein incorporated by reference.

An especially preferred prokaryotic vector is one that, in lieu of expressing the entire SpA protein, expresses only the IgG-binding domains of the protein. Thus, such vectors express the protein fused to only a portion of SpA. Most preferably, such vectors will be constructed such that the expressed fusions will contain a cleavable site located between the IgG-binding domains and the desired protein. Examples of such vectors are described by Nilsson, B. et al. (*Meth. Enzymol.* 398:3–16 (1990)), herein incorporated by reference. A particularly preferred example of such a vector is pEZZ18 and its derivatives having cleavable sites (Nilsson, B. et. al., *Meth. Enzymol.* 198:3–16 (1990)). The pEZZ18 vector contains a lacZ gene sequence fused to the SpA IgG-binding domains. The lacZ sequences are separated from the IgG domains by a multi-linker site, such that a desired DNA fragment can be readily inserted into the vector. The insertion of a desired sequence alters or obliterates the expression of the LacZ protein, and hence can be detected using chromogenic substrates (Nilsson, B. et al., *Meth. Enzymol.* 198:3–16 (1990)).

If desired, however, yeast and fungal vectors may be used. Examples of suitable yeast vectors include the yeast 2-micron circle, the expression plasmids YEP13, YCP and YRP, etc., or their derivatives. Such plasmids are well known in the art (Botstein, D., et al., *Miami Wntr. Symp.* 19:265–274 (1982); Broach, J. R., In: *The Molecular Biology of the Yeast Saccharomyces: Life Cycle and Inheritance,* Cold Spring Harbor Laboratory, Cold Spring Harbor, N.Y., p. 445–470 (1981); Broach, J. R., *Cell* 28:203–204 (1982); Sambrook, J. et al., In: Molecular Cloning, A Laboratory Manual, 2nd Ed., Cold Spring Harbor Press, Cold Spring Harbor, N.Y. (1989)).

If alternatively desired, the inhibitors of the present invention may be produced by expression in mammalian cells, using eukaryotic vectors (especially, a eukaryotic viral or retroviral vector). Typically, such vectors will be designed to include a prokaryotic replicon, and selectable marker, such that the propagation of the vector in bacterial cells can be readily accomplished. In order to replicate in mammalian cells, however, the vectors will also contain a viral replicon, such as the replicon of Epstein-Barr virus, bovine papilloma virus, parvovirus, adenovirus, or papovavirus (i.e. SV40 or polyomavirus).

Plasmid vectors using papovavirus replicons ultimately kill their host cells, and are thus preferred for transient expression. SV40-based vectors that may be used include pMSG (Pharmacia), pSVT7, pMT2 (Kaufman, R. J., In: Genetic Engineering: Principles and Methods Vol. 9 (Setlow, J. K., Ed.) Plenum Publishing, N.Y. (1987)).

In contrast, vectors that employ the replicons of Epstein-Barr, or bovine papilloma viruses do not generally cause cell death, and are thus suitable for long term propagation. Examples of such vectors include BPV-1, pBV-1MTHA, pHEBo, p205 (Shimuzu, Y. et al., *Mol. Cell. Biol.* 6:1074 (1986); Kioussis, D. et al. *EMBO J.* 6:355 (1987); Sambrook, J. et al., *EMBO J.* 4:91 (1985).

Sambrook, J. et al., herein incorporated by reference, provide a review of the characteristics of mammalian vectors (In: *Molecular Cloning, A Laboratory Manual,* 2nd Ed., Cold Spring Harbor Press, Cold Spring Harbor, N.Y. (1989).

The use of recombinant DNA expression methods facilitates the isolation and recognition of additional inhibitor molecules. In one embodiment, such molecules can be subjected to random mutagenesis (see, for example, Watson, J. D. et al., *Molecular Biology of the Gene,* Fourth Edition, Benjamin/Cummings, Menlo Park, Calif. (1987)). Significantly, a random mutagenesis approach requires no a priori information about the protein encoded by the gene that is to be mutated. This approach has the advantage that it assesses the desirability of a particular mutant on the basis of its function, and thus does not require an understanding of how or why the resultant mutant protein has adopted a particular conformation. Indeed, the random mutation of target gene sequences has been one approach used to obtain mutant proteins having desired characteristics (Leatherbarrow, R. J. *Prot. Eng.* 1:7–16 (1986); Knowles, J. R., *Science* 236:1252–1258 (1987); Shaw, W. V., *Biochem. J.* 246:1–17 (1987); Gerit, J. A. *Chem. Rev.* 87:1079–1105 (1987)).

The efficiency of the mutagenesis can be increased by recognizing that the identity and location of critical or key amino acid residues has been determined by virtue of the isolation and sequencing of the above-described mutants. Thus, it is possible to use site-specific mutagenesis techniques to selectively alter only those amino acids of the protein that are believed to be important (Craik, C. S., *Science* 228:291–297 (1985); Cronin, C. S. et al., *Biochem.* 27:4572–4579 (1988); Wilks, H. M. et al., *Science* 242:1541–1544 (1988)). Once the population of mutants has been obtained, each mutant must be analyzed to determine whether it fulfills the desired criteria. This analysis can be facilitated through the use of a phage display protein ligand screening system (Lowman, H. B. et al., Biochem. 30:10832–10838 (1991); Markland, W. et al., *Gene* 109:13–19 (1991); Roberts, B. L. et al., *Proc. Natl. Acad. Sci. (U.S.A.)* 89:2429–2433 (1992); Smith, G. P., *Science* 228:1315–1317 (1985); Smith, R. P. et al., *Science* 248:1126–1128 (1990), all herein incorporated by reference)). In general, this method involves expressing a fusion protein in which the desired protein ligand is fused to the C-terminus of a viral coat protein (such as the M13 Gene III coat protein, or a lambda coat protein).

IV. Uses of the Inhibitors of the Present Invention

The present invention provides inhibitors of urokinase and similar proteases. A preferred class of such inhibitors comprise "low molecular weight" "proteinaceous" inhibitors. As used herein, an inhibitor is said to be proteinaceous if it is a protein or polypeptide, or a derivative of either. A proteinaceous inhibitor is said to be of "low molecular weight" if the proteinaceous portion of the inhibitor has a molecular weight of less than 20,000, and more preferably less than 15,000. Such desired inhibitors are exemplified by the mutated OM3TKY molecules 88, 89, 90 and 91 described above.

Such inhibitors may be modified so as to contain or lack one, two, or several amino acids from either the amino or carboxyl terminus. Similarly, equivalent amino acids can be used anywhere in the protein in lieu of those designated. As is known in the art, the amino acids may be present in either their protected or unprotected forms, using appropriate amino or carboxyl protecting groups. The molecule may have a free amine on its amino terminus, or it may be prepared as an acid-addition salt, or acetylated derivative. Examples of functionally active protein and peptide analogues and functional derivatives, and methods for their preparation are disclosed in U.S. Pat. Nos. 4,605,641 (Bolin et al.); 4,734,400 (Bolin et al.); 4,822,774 (Ito et al.); 4,835,252 (Musso et al.); 4,939,224 (Musso et al.); 5,055,302 (Laties et al.), all herein incorporated by reference).

As indicated above, urokinase plays an important role in a variety of physiological processes in which the degradation of tissue occurs. Such processes include, for example, the translation of tumor cells from the site of a primary tumor to putative metastatic sites, the degradation of mammary tissue following lactation, the process of ovulation, and the process through which fertilized ova become implanted in the uterine wall at the onset of pregnancy. Urokinase plays a role in effecting the release of the oocyte from the follicle. Thus, urokinase inhibitors can prevent pregnancy by impairing or preventing such release.

A use is said to be therapeutic if it alters a physiologic condition in a desirable manner. The agents of the present invention may be used locally or systemically to prevent or attenuate any "urokinase-dependent" process. As used herein, a "urokinase-dependent" process is any physiological process or reaction that involves and is facilitated by urokinase, or a similar protease. The inhibitors of the present invention thus can be used in cancer therapy to prevent or attenuate the metastatic potential of a tumor. They can be used to prevent pregnancy in females by either preventing ovulation, or by impairing the capacity of the fertilized ova to implant itself into the uterine wall.

The agents of the present invention may be administered systemically. Such administration is preferred, for example, in the treatment or prevention of metastasis. Such administration may, for example, be by parenteral, intravenous, or intranasal means. In some embodiments, such as in the prevention of pregnancy, topical or local administration is preferred.

The agents of the present invention can be administered in either a "prophylactic" or "therapeutic" manner. An agent that is administered in a prophylactic manner is provided in advance of any identified need (for example, as a contraceptive agent, or prior to the detection of a potentially metastatic tumor). The administration of such a compound serves to prevent or attenuate any urokinase-dependent process. In contrast, an agent that is administered in a therapeutic manner is provided at (or after) the onset of a symptom of a urokinase-dependent process (such as, for example, the detection of a metastasis). The administration of such a compound serves to attenuate the consequences of the urokinase-dependent process (such as, for example, attenuating the clinical significance, grade, size, number or consequence of the metastasis).

The therapeutic agents of the present invention can be formulated according to known methods used to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in Remington's Pharmaceutical Sciences (16th ed., Osol, A., Ed., Mack, Easton Pa. (1980)). In order to form a pharmaceutically acceptable composition suitable for effective administration, such compositions will contain an effective amount of such agents, together with a suitable amount of carrier vehicle.

Additional pharmaceutical methods may be employed to control the duration of action. Controlled release preparations may be achieved through the use of polymers to complex or absorb the agents. The controlled delivery may be exercised by selecting appropriate macromolecules (for example polyesters, polyamino acids, polyvinyl pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled release preparations is to incorporate the agents into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatin-microcapsules and poly(methylmethacylate) microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

In one embodiment, the inhibitors of the present invention can be joined to one or more additional moieties, including non-proteins or domains of other proteins. Such joining may result from a conjugation of the inhibitor molecules with the other molecule(s). Any of a variety of methods can be used to effect such conjugation. For example, such conjugation may be achieved by covalently modifying the inhibitor molecules with a bivalent adduct or "crosslinking agent" (such as glutaraldehyde, succinic anhydrides, etc.). Alternatively, such conjugation may be achieved through the exploitation of ligand interactions. For example, the affinity of biotin for avidin can be exploited to fashion biotinylated derivatives that can be joined to one another via avidin, avidin derivatives, or mercurated compounds.

In another embodiment, the joining of the inhibitors of the present invention to domain(s) of other molecules, especially proteins, can be accomplished using recombinant methods. In this embodiment, a nucleic acid molecule is employed that, upon expression, yields an inhibitor molecule of the present invention as a fusion protein, covalently bound (via a peptide bond, or an amino acid or polypeptide bridge) to the domain(s) of interest.

The inhibitors of the present invention can thus be joined to domain(s) of other proteins, such as antibodies or receptor ligands or receptor molecules, or to non-proteins. Preferred classes of protein molecules include receptor ligands, and especially ligands that are capable of specific or preferential binding to tumor cells. In this manner, the conjugate protein can facilitate the transport of the inhibitor to the site of the tumor. A particularly preferred ligand conjugate is the cellular urokinase receptor ligand. The urokinase receptor is universally present in and on tumor cells, especially on cells of the leading (or metastatic) edge of a tumor mass. In view of such universal presence, the use of a urokinase receptor ligand would permit a single molecule to be used against all tumor types. In such an embodiment, the urokinase inhibitor could preferentially bind to those cells that have arrayed the urokinase receptor. In contrast, if one were to use tumor-specific antigens as a target, it would be necessary to develop a library of tumor antigen-specific antibodies.

In an alternative embodiment, "humanized" antibodies (i.e. non-human antibodies which are non-immunogenic in a human) can be used as the conjugate protein. Methods for producing such antibodies are well known (Robinson, R. R. et al., International Patent Publication PCT/US86/02269; Akira, K. et al., European Patent Application 184,187; Taniguchi, M., European Patent Application 171,496; Morrison, S. L. et al., European Patent Application 173,494; Neuberger, M. S. et al., PCT Application WO 86/01533; Cabilly, S. et al., European Patent Application 125,023).

Whereas, in a preferred embodiment, the inhibitor molecules of the present invention are provided per se to a recipient, the invention also contemplates the administration of DNA or RNA molecules that encode and express the inhibitor molecules as a method of gene therapy. In such an embodiment of the present invention, DNA encoding an inhibitor is introduced into the somatic cells of an animal (particularly mammals including humans) in order to provide a treatment for cancer (i.e. "gene therapy"). Most preferably, viral or retroviral vectors are employed for this purpose.

The principles of gene therapy are disclosed by Oldham, R. K. (In: Principles of Biotherapy, Raven Press, NY, 1987), and similar texts. Disclosures of the methods and uses for gene therapy are provided by Boggs, S. S. (Int. J. Cell Clon. 8:80–96 (1990)); Karson, E. M. (Biol. Reprod. 42:39–49 (1990)); Ledley, F. D., In: *Biotechnology, A Comprehensive Treatise*, volume 7B, Gene Technology, VCH Publishers, Inc. NY, pp 399–458 (1989)); all of which references are incorporated herein by reference.

Although, as indicated above, such gene therapy can be provided to a recipient in order to treat (i.e. suppress, or attenuate) an urokinase-dependent process, the principles of the present invention can be used to provide a prophylactic gene therapy to individuals who, due to inherited genetic mutations, somatic cell mutation, or pre-diagnosed medical condition, have an enhanced probability of cancer, etc.

Having now generally described the invention, the same will be more readily understood through reference to the following examples which are provided by way of illustration, and are not intended to be limiting of the present invention, unless specified.

EXAMPLE 1

Mutagenesis of Turkey Ovomucoid Third Domain Gene sequences that encode the turkey ovomucoid third domain (OM3TKY) were mutagenized using plasmid, pEZZ318TKYMET, which is a variant of the expression plasmid pEZZ318. The plasmid contains an fl ori site, and an ampicillin resistance determinant. The plasmid is capable of mediating the expression of OM3TKY as a fusion protein, in which the OM3TKY sequences are fused to the C-terminus of two tandem protein A domains. The expressed fusion protein has been engineered to contain a cyanogen bromide cleavage site at the amino terminus of OM3TKY. Thus, after synthesis, the fusion protein can be readily cleaved to yield the desired OM3TKY sequences free of additional protein. The recombinant protein expressed in *E. coli*, prior to chemical cleavage has the sequence (SEQ ID NO:1):

```
AAQHDEAVDNKFNKEQQNAFYEILHLPNLNEEQRNAFIQSLKDDPSQSA
NLLAEAKKLNDAQAPKVDNKFNKEQQNAFYEILHLPNLNEEQRNAFIQS
LKDDPSQSANLLAEAKKLNDAQAPKVDRKEAHFAMVDCSEYPKPACTLE
YRPLCGSDNKTYGNKCNFCNAVVESNGTLTLSHFGKC
```

After cleavage (at the underlined methionine), the above sequence comprising the turkey ovomucoid third domain is obtained (SEQ ID NO:2):

```
VDCSEYPKPACTLEYRPLCGSDNK-
    TYGNKCNFCNAVVESNGTLTLSHFGKC
```

In accordance with the above-described methods, site specific mutagenesis was used to introduce mutations into a gene sequence that encodes the OM3TKY protein. Four different oligonucleotides were used to mutagenize the five codons around the coding region for the ovomucoid active site. These oligonucleotides are:

1) The PAI-2 derived mutant, 88 (SEQ ID NO: 3): gtt gtc gga Gcc aca gag agg ATG TCC CGT TCG TCC gca tgc agg
2) The PAI-1 derived mutant, 89 (SEQ ID NO:4): gtt gtc gga Gcc aca gag agg TGC TGC CAT TCG TGC gca tgc agg
3) The Plasminogen derived mutant, 90 (SEQ ID NO:5:): gtt gtc gga Gcc aca gag agg TCC AAC AAC TCG TCC gca tgc agg
4) The Nexin-1 derived mutant, 91 (SEQ ID NO:6): gtt gtc gga Gcc aca gag agg TGC GGA GGA TCG TGC gca tgc agg The regions of mutagenesis are shown in capital letters. At position 10 from the 5' end of each oligonucleotide, there is a mutation which eliminates a unique BamHI site in pEZZ318TKY-MET, which facilitates screening for mutants.

The oligonucleotides were kinased with T4 polynucleotide kinase, and then single primer oligonucleotide-directed mutagenesis was done on single stranded pEZZ318TKY-MET with a 15-fold molar excess of primer to template. T4 ligase was added to the oligonucleotide-template reaction mixture (including DTT and ATP), then dNTPs, and Klenow fragment (Amersham) were added. Polymerization was allowed to proceed for 17 hours at 16° C. The reaction was transformed into competent mut1 cells, and then grown in 5 ml liquid culture LB media+ampicillin (100 µg/ml) at 37° C. for 16 hours. Double-stranded DNA was prepared from the 5 ml growths by a simplified procedure of the alkaline-lysis plasmid preparation method (Sambrook, J., et al., Molecular Cloning, A Laboratory Manual, Cold Spring Harbor Press, Cold Spring Harbor, N.Y. (1989)).

After the plasmid DNA was re-dissolved in TE, 2 µl was used in a BamHI digestion. After two hours of digestion, 2 µl of each BamHI reaction was transformed into JM109 competent cells, plated onto LB agar+ampicillin plates, and grown overnight at 37° C. Colonies from these plates were selected, grown and screened for BamHI resistance. The BamHI digestion was carried out at 37° C. for 90 minutes in a total volume of 10 µl, using 1 µl BRL BamHI, and 1 µl BRL React 3 Buffer(10×). Resistance to BamHI digestion was determined by running the digests on a 1% agarose gel (agarose in Tris-Acetate-EDTA buffer). The BamHI resistant samples were sequenced by the dideoxy chain termination method. From the sequences, the desired four mutants were identified, and used for expression of the mutant proteins.

The four inhibitor molecules thereby produced have the amino acid sequences (the differences between the sequences are indicated by underscoring):

(100 µg/ml) overnight at 37° C. These cultures were centrifuged at 6000 rpm in an SS-34 rotor for ten minutes, and the supernatant was discarded. The pellets were resuspended in 25 ml 2×YT each, and used to inoculate 1 liter growths in 2×YT+ampicillin (100 µg/ml), which were grown for 4 hours at 37° C. The one liter cultures were then cooled down in an ice-water bath for 30 minutes. These growths were then centrifuged at 8000 rpm in a GS-3 rotor for 15 minutes at 4° C. The supernatant was discarded, and the pellets frozen overnight at −20° C.

The frozen pellets were thawed, and resuspended in 25 ml cold sucrose buffer (0.5M sucrose, 0.2M Tris-HCl (pH 8.2), 1 mM EDTA). After sitting for 10 minutes in an ice water bath, 0.5 g of lysozyme was added to each resuspension, immediately followed by 25 ml of ice cold distilled water. This mixture was vortexed thoroughly, and then incubated in an ice-water bath for 5 minutes. 1 ml of 1M $MgSO_4$ was added to each lysate, and the lysates were centrifuged in Oak Ridge tubes at 12000 rpm in an SS-34 rotor for 20 minutes. The supernatants from each tube were filtered through a 0.45 micron filter, and if not immediately taken for further purification, were frozen at −20° C. until further use.

Affinity purification of proteins from each osmotic shock supernatant was done on IgG-sepharose (Pharmacia) gels of 3–4 ml bed volume. The columns were equilibrated with a 10×bed volume of TST (50 mM Tris-HCl (pH 7.4), 150 mM NaCl, 0.05% Tween 10) before loading the osmotic shock supernatants. The columns were then washed with 300 ml of TST. The buffer capacity of the column was then lowered by washing with 15 ml of 1 mM ammonium acetate. The columns were eluted with 10 ml of 0.5M acetic acid titrated to pH 3.2 with ammonium acetate. The eluates were collected in 10 ml of 1 M Tris-HCl (pH 8.0), and frozen at −70° C. When completely frozen, the samples were lyophilized. Lyophilized samples were re-dissolved in 2 ml distilled water and frozen until further use.

SDS-PAGE was routinely used as a check on the expression and purification procedures. A 12.5% polyacrylamide gel was used to resolve the proteins in the IgG eluate, which was stained with Coomasie blue, and destained with methanol/acetic acid. The major bands after purification corresponded in apparent molecular weight to the Protein A-ovomucoid third domain fusion protein and a breakdown product of two Protein A domains.

---

88 (SEQ ID NO: 7):
VDCSEYPKPAC<u>GRTGHP</u>LCGSDNKTYGNKCNFCNAVVESNGTLTLSHFGKC
89 (SEQ ID NO: 8):
VDCSEYPKPAC<u>ARMAA</u>PLCGSDNKTYGNKCNFCNAVVESNGTLTLSHFGKC
90 (SEQ ID NO: 9):
VDCSEYPKPAC<u>GRVVG</u>PLCGSDNKTYGNKCNFCNAVVESNGTLTLSHFGKC
91 (SEQ ID NO: 10):
VDCSEYPKPAC<u>ARSSA</u>PLCGSDNKTYGNKCNFCNAVVESNGTLTLSHFGKC

---

EXAMPLE 2

Protein Expression and Purification

Protein expression of the mutagenized pEZZ-derived plasmids of Example 1 was carried out in JM109 cells, and the protein was harvested by an osmotic shock procedure. A 100 ml culture of cells containing the plasmid expressing the wild type or mutant gene was grown in 2xYT + ampicillin

EXAMPLE 3

Quantification of Urokinase

In order to quantitate UK activity, a method of back titration from quantitated trypsin was used with a calibrated chloromethyl ketone (CK) inhibitor (Magnotti, R. A. et al., Anal. Biochem. 170:228–237 (1988)). The difference in enzyme activity between inhibited and non-inhibited enzymes, as determined by change in absorbance over time at 405 nm, was used to calculate chloromethyl ketone concentration. From this calibrated CK concentration, the concentration of urokinase was readily determined using the formula:

$$[CA] = ([Enzyme] \times (1 - Fractional\ Residual\ Activity))$$

Fractional residual activity is the ratio of enzyme activity with CK in the reaction to enzyme activity without CK in the reaction.

Titration of trypsin active sites was done using the burst titrant p-nitrophenyl p-guanidinobenzoate (Chase T. et al., *Biochem. Biophys. Res. Commun.* 29:508–614 (1967)). The reaction was performed in Buffer A (50 mM Hepes, 20 mM $CaCl_2$, 0.1% PEG 8000, at pH8.0 (Magnotti, R. A. et al., *Anal. Biochem.* 170:228–237 (1988)). Titrations were performed with a trypsin solution containing 2 mg/ml Bovine Trypsin (Type III Sigma), using 50, 80 and 100 μl of this stock solution. The bursts were read at 410 nm on a Uvikon 860 spectrophotometer in plastic cuvettes with a path length of 1 cm. The trypsin solution used was determined to be $5 \times 10^{-4}$M.

Determination of urokinase active site concentration was done by a back titration with an arginyl specific chloromethyl ketone (EGRCK: L-glutamyl-glycyl-arginyl-chloromethyl ketone from Calbiochem) active against UK and trypsin (Magnotti, R. A. et al., Anal. Biochem. 170:228–237 (1988)).

This chloromethyl ketone was first calibrated against a known concentration of trypsin in Buffer A using the chromogenic substrate BAPNA (Sigma), and determined to be at a concentration of $2.6 \times 10^{-5}$M. The UK determination was done in Buffer C (50 mM Tris-HCl, 0.1M NaCl, 0.01% Tween 80, all at pH 8.0), using chromogenic substrate S-2288 (KabiGen) at 1 mM concentration.

Protein samples were assayed to determine whether any of the mutants exhibited UK inhibitory activity. "Abbokinase" (Urokinase for Injection-Abbott Pharmaceuticals) was dissolved in distilled water and assays were done in a solution containing 0.05% mannitol, 0.5% human albumin, and 0.1% NaCl.

Figure 2A:
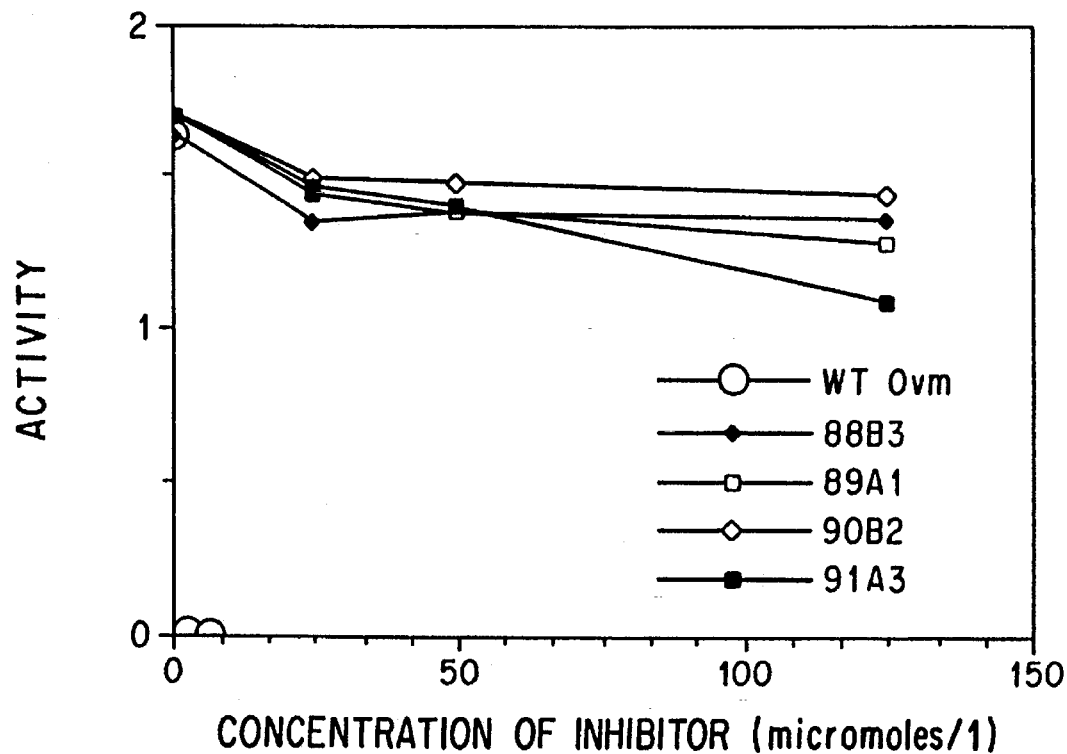
FIG. 2 shows plots of initial crude assays to determine inhibitory activity of inhibitor constructs. The numbers in the legends refer to the oligonucleotide numbers. Absorbance at 405 nm and activity were determined in a Kontron Uvikon 860 spectrophotometer. The top panel shows chymotrypsin activity versus inhibitor concentration in μM. Chymotrypsin concentration was 0.1 μM. The lower panel shows urokinase activity versus inhibitor concentration in μM. Urokinase concentration was 1.6 μM.
Figure 2B:
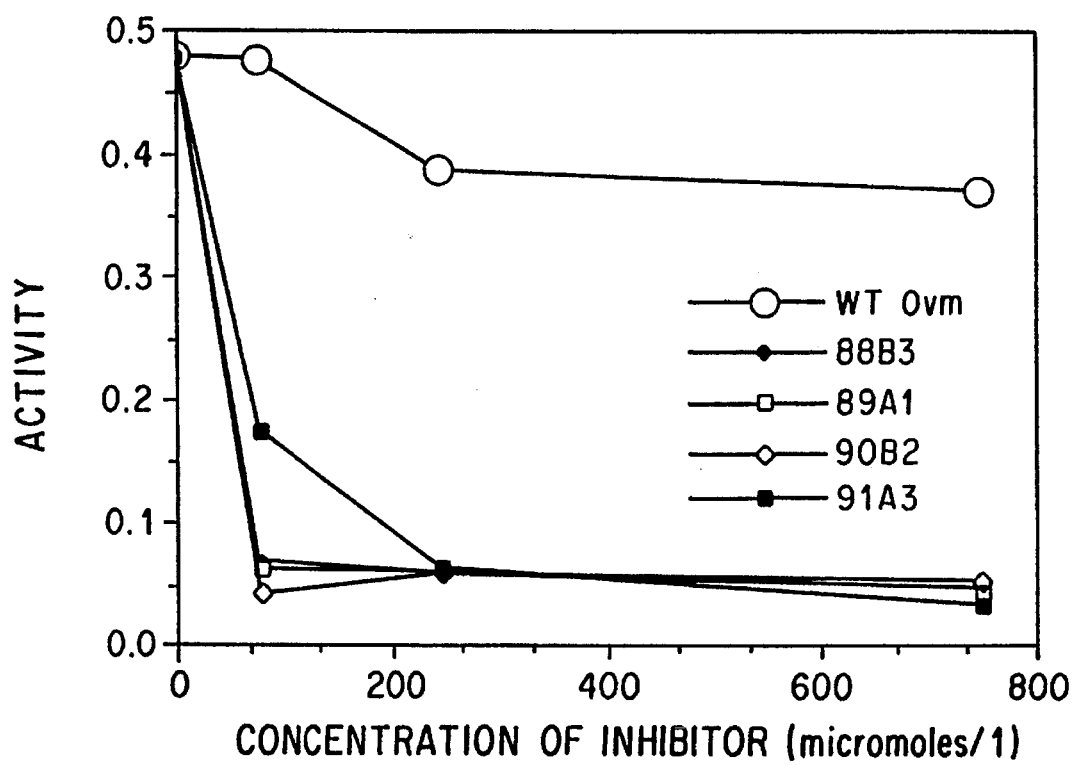
Figure 3A:
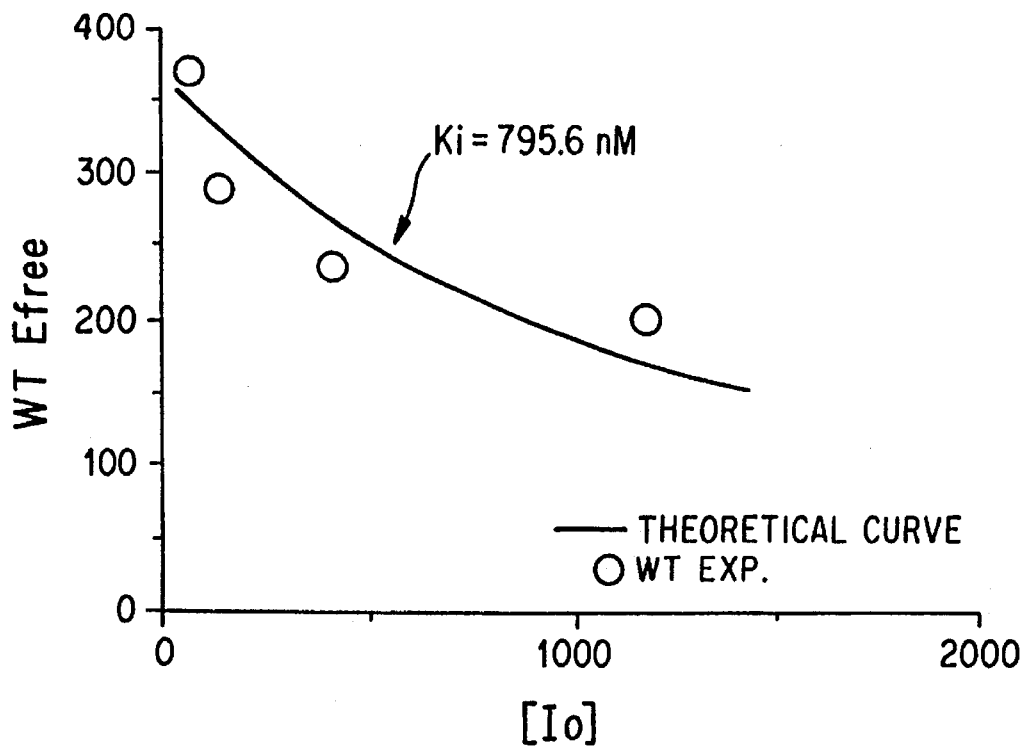
FIGS. 3A–3F show plots of inhibitor concentration (in nM) versus free urokinase (in nM). The experimental data (open circles is plotted against the theoretical curve (solid line) for an inhibitor for the given $K_i$ value. The $K_i$ values were determined using Enzfitter (Elsevier Biosoft). The data is presented for wild-type "WT" inhibitor (FIG. 3A) and for five mutant inhibitors: "Arg18" (FIG. 3B), "88" (FIG. 3C), "89" (FIG. 3D), "90" (FIG. 3E) and "91" (FIG. 3F).
Figure 3B:
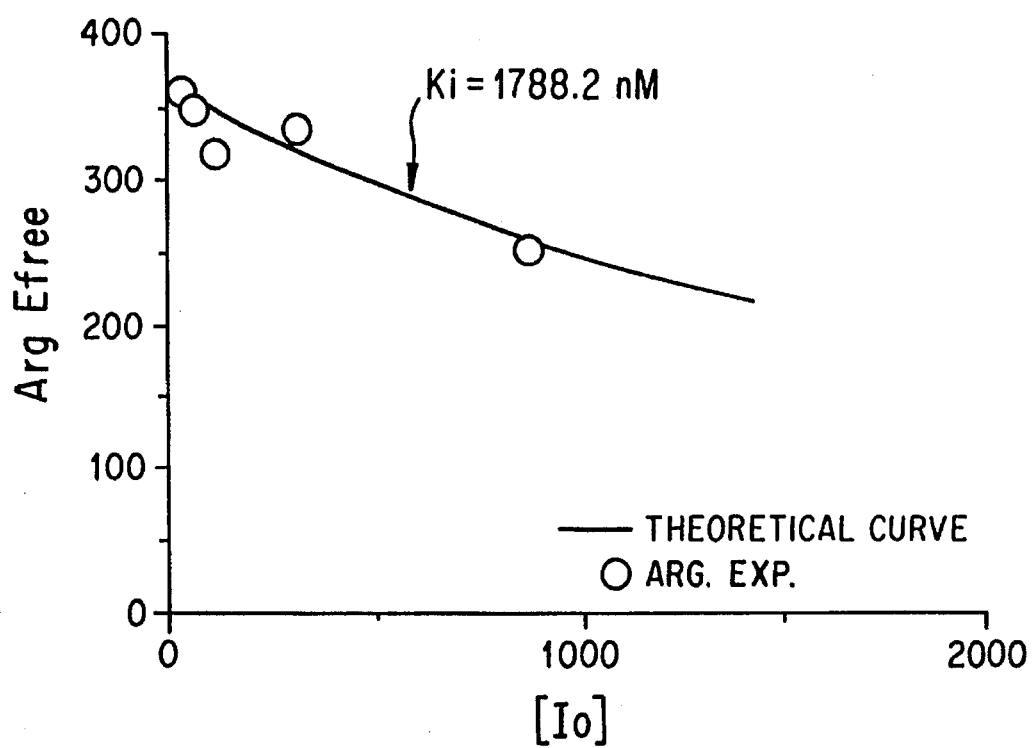
Figure 3C:
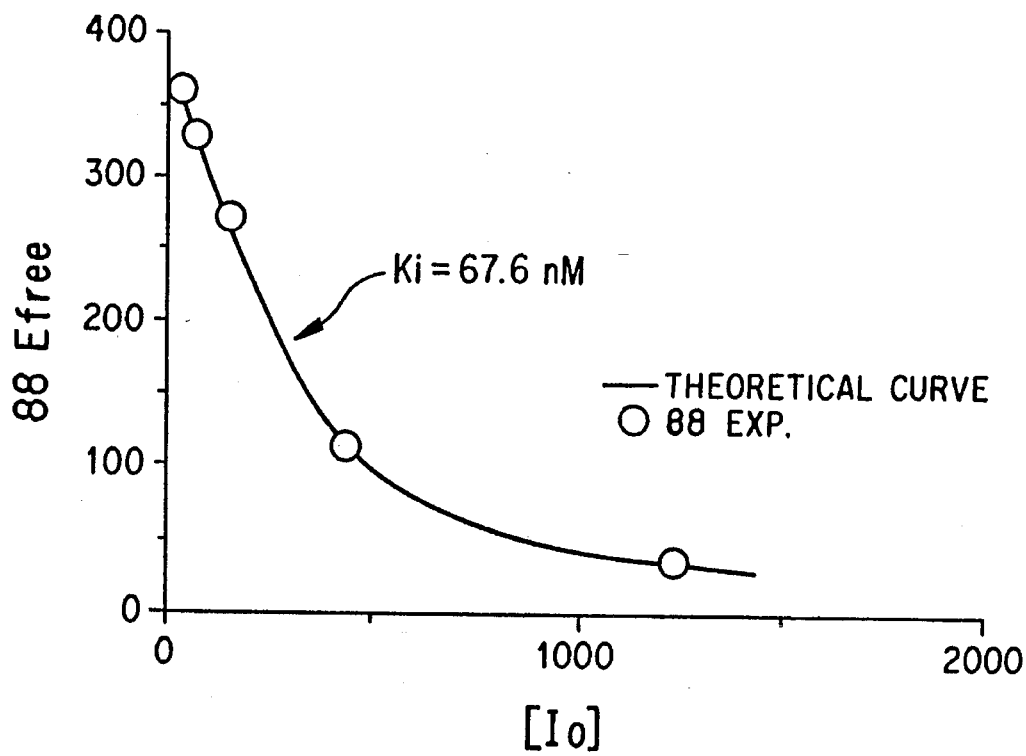
Figure 3D:
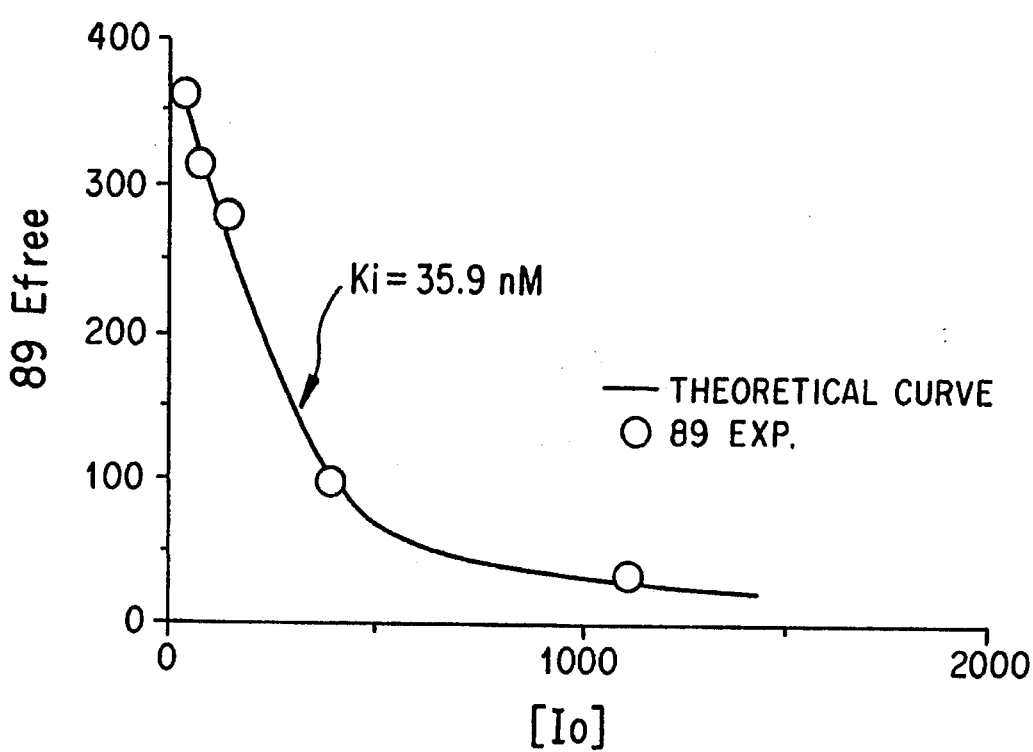
Figure 3E:
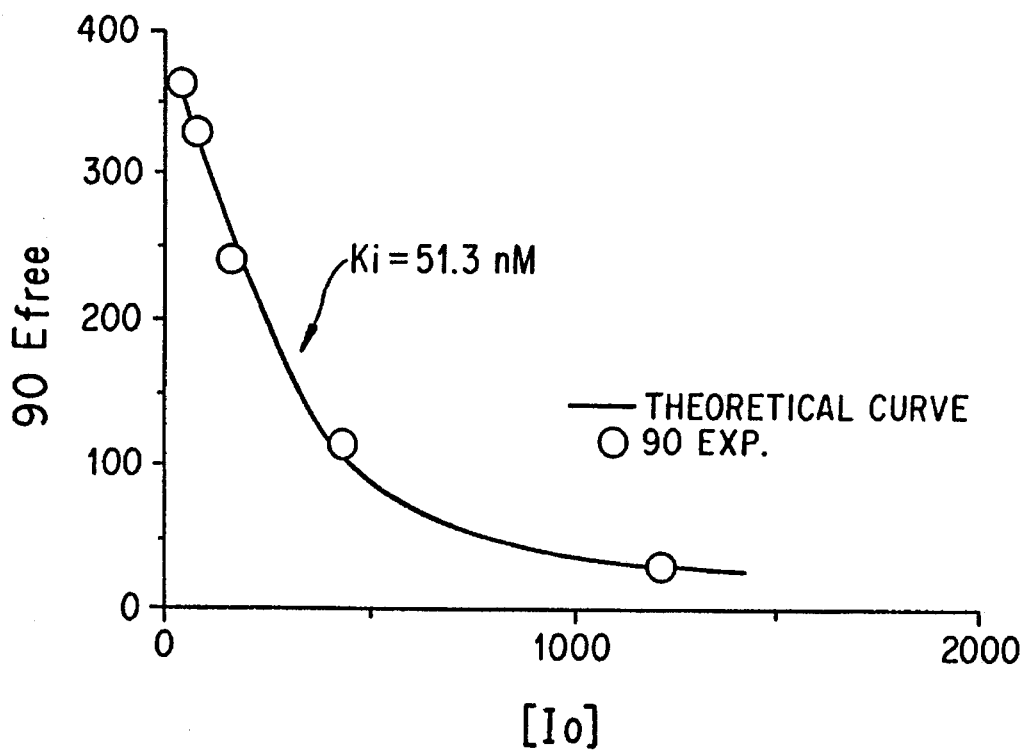
Figure 3F:
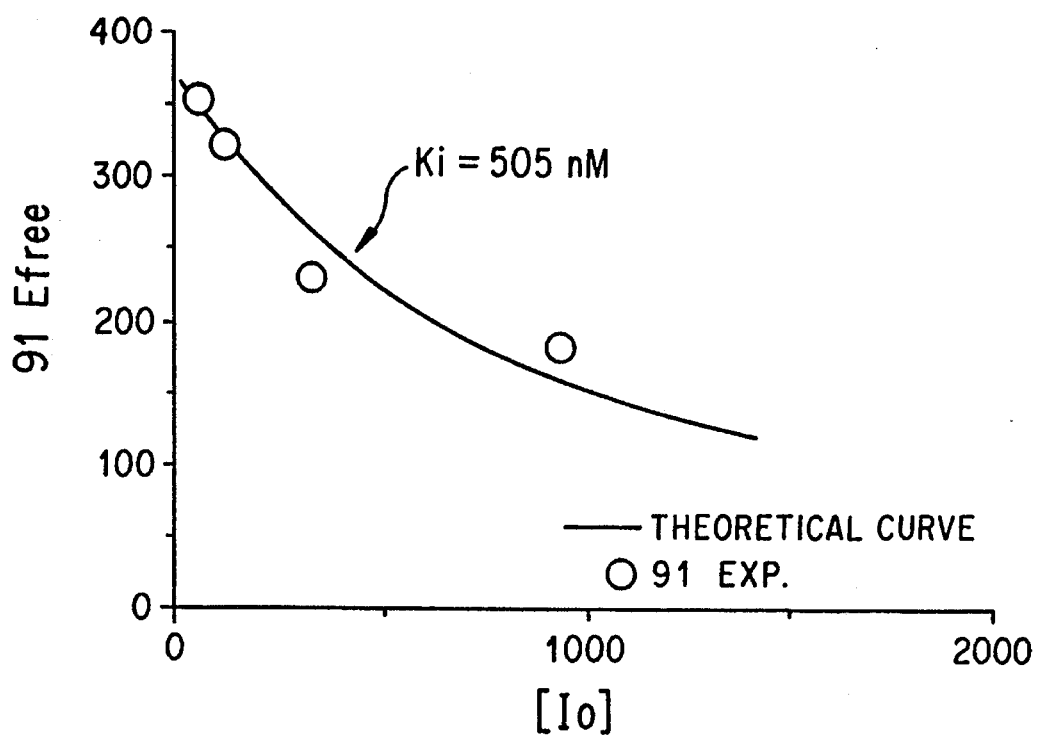

The results of this experiment are shown in FIG. 2. In the top panel of FIG. 2, the activity (change in absorbance at 405 nm/minute) of chymotrypsin is plotted. The lower panel of FIG. 2 provides a similar plot of the activity of UK. Inhibitor concentration is expressed as moles of inhibitor per moles of enzyme active site, and based on bichoncinninic acid quantification of protein in the samples, and concentration of wild-type inhibitor titrated against known chymotrypsin concentrations. Substrate concentration in each reaction is 2 times $K_m$.

The results (FIG. 2, top panel) show a loss of chymotrypsin inhibitory function in the mutants. The results show that the mutants are able to inhibit UK to a much greater degree than can wild type OM3TKY (FIG. 2, lower panel).

EXAMPLE 4 1

Determination of $K_m$ for Mutant Inhibitors

Fractional enzyme activities for each inhibitor-UK interaction of the above discussed inhibitors were determined by the assay method of Empie and Laskowski (Empie, M. W. et al., *Biochem.* 21:2274–2284 (1982)), as adapted from Green and Work (Green, N. M. et al., Biochem. J. 54:347–352 (1953)). The concentration of UK used for these reactions was 35 nM. The reactions were carried out in Buffer C. The concentration of the chromogenic substrate used with UK in these assays (S-2288, KabiGen) was 50 μM, which is one tenth of the $K_m$ of the substrate for UK. $K_m$ was determined by a Michaelis-Menten analysis, using a 100-fold range of substrate concentration in Buffer C, and determined to be $4 \times 10^{-4}$M. $K_i$ values were calculated as the slope of a plot of $[I]_o/(1-a)$ vs. 1/a ("a" represents residual enzyme activity) using a variation of the formulas derived by Henderson (Pratt, C. W. et al., Biochem. 26:2855–2863 (1987)). Table 5 shows the $K_i$ values obtained for the wild type OM3TKY, and five mutants. These five mutants include the four detailed above (88, 89, 80, AND 91), and also a mutant with arginine at the P1 site of OM3TKY (P1-Arg). As is shown in the Table, wild type OM3TKY and the P1 Arg mutant displayed virtually no inhibitory activity against UK. The values for PSTI, PAI-1, PAI-2, and Nexin-1 were obtained from Turpeinen, U. et al. (*Biochem. J.* 254:911–914 (1988)), Kruithof, C.K.O. et al. (Thromb.-Haemost. 55::65–68 (1986)), Christensen, U. et al. (Thromb.-Haemost. 48:24–26 (1982)), and Stein, P. E. et al. (*Nature* 347:99–102 (1990)), respectively. "ND" means not determined. $K_i$ values for serpins are not functionally comparable to those of reversible inhibitors.

TABLE 5

| $K_i$ VALUES FOR INHIBITORS AGAINST UK ||
| Inhibitor | $K_i$ (nM) |
| --- | --- |
| WT-OM3TKY | — |
| P1-Arg | — |
| 88 | 40 |
| 89 | 0.31 |
| 90 | 106 |
| 91 | 120 |
| PSTI | 300 |
| PAI-1 | ND |
| PAI-2 | <<.01 |
| Nexin-1 | ND |

The $K_i$ values in the above table support the validity of the initial modelling and changes to the Kazal system, and indicate that modelling can be used to yield urokinase inhibitors.

$K_i$ values for the wild-type and mutant inhibitors versus urokinase were also determined by non-linear regression of the following equation:

$$E = E_0 - \frac{(E_0 + I_0 + K_i) - \sqrt{(E_0 + I_0 + K_i)^2 - 4E_0 I_0}}{2}$$

The non-linear regression was done using the program Enzfitter, by Robin Leatherbarrow. $E_o$ represents a total enzyme concentration in the reaction, $I_o$ represents total inhibitor concentration, E is the free enzyme for a given inhibitor concentration and $K_i$ is the equilibrium constant for the inhibitor. E and $K_i$ are the unknowns in the equation, and are solved for during the regression analysis. Enzyme and inhibitor concentrations used were determined as mentioned above. Using this method, the $K_i$ values (in nM) reported in Table 6 were determined.

TABLE 6

K$_i$ VALUES OBTAINED BY NON-LINEAR REGRESSION FOR INHIBITORS AGAINST UK

| Inhibitor | K$_i$ (nM) |
| --- | --- |
| WT-OM3TKY | 795.6 ± 260 |
| P1-Arg | 1788.2 ± 415 |
| 88 (PAI-2 derived Mutant) | 67.6 ± 5.6 |
| 89 (PAI-1 derived Mutant) | 35.9 ± 10.5 |
| 90 (Plasminogen derived Mutant) | 51.3 ± 15.2 |
| 91 (Nexin derived Mutant) | 505 ± 122 |
| PSTI | 300 |

The data for wild-type, and the "Arg18," "88," "89", "90," and "91" mutants are shown graphically in FIGS. 3A–3F.

EXAMPLE 5

Differences in the P2-P4,' Regions of the Mutant Inhibitors

The differences between the P2-P4' regions in the above-described inhibitors is shown in Table 7. The Table provides a sequence comparison of the four engineered mutants, native Pancreatic Secretory Trypsin Inhibitor (PSTI), and the natural inhibitors to UK. PSTI, a Kazal-type inhibitor from humans, was included in Table 7 because it had been reported that PSTI (identified as TATI), had some affinity to UK (Turpeinen, U. et al. (*Biochem, J.* 254:911–914 (1988)).

TABLE 7

SEQUENCE COMPARISON OF P2-P4' IN UK INHIBITORS

| P2 | P1 | P1' | P2' | P3' | P4' | INHIBITOR |
| --- | --- | --- | --- | --- | --- | --- |
| T | L | E | Y | R | P | OM3TKY |
| T | R | E | Y | R | P | P1 ARG |
| G | R | V | V | G | P | PLASMINOGEN DERIVATIVE (90) |
| G | R | T | G | H | P | PAI-2 DERIVATIVE (88) |
| A | R | M | A | A | P | PAI-1 DERIVATIVE (89) |
| A | R | S | S | A | P | NEXIN-1 DERIVATIVE (91) |
| A | R | M | A | P | E | PAI-1 |
| G | R | T | G | H | G | PAI-2 |
| G | R | V | V | G | H | PLASMINOGEN |
| A | R | S | S | P | P | NEXIN-1 |
| T | K | I | Y | N | P | PSTI |

Unlike PSTI, all of the mutant inhibitors created by the methods of the present invention, and all the natural inhibitors to UK, have a glycine or alanine at P2, which might be adding to the flexibility of the P1 loop. Such flexibility may be desirable for UK inhibition in that it appears that more flexibility in the P1 loop of Kazal and Kunitz inhibitors might work to increase their inhibitory effects against plasminogen activators. Structural studies of ovalbumin, a non-inhibitory serpin, and the closest sequence homologue to PAI-2, has shown a reactive center (P1 loop) in the shape of an a-helix (Stein, P. E. et al. (*Nature* 347:99–102 (1990)). In inhibitory serpins, recent studies have shown that this reactive center loop is extremely mobile (Carrell, R. W. et al., *Nature* 353:576–578 (1991)), with the serpin having to be forced into an energetically unstable position that exposes a large portion of P10-P14'. Increased exposure to proteolysis is often viewed as a measure of increased flexibility and movement in a protein segment (Onesti, S. et al., *J. Molec. Biol.* 217:153–176 (1991)).

Studies on soybean-type trypsin inhibitors from Erythrina seeds shows that it has affinity for t-PA (Onesti, S. et al., *J. Molec. Biol.* 217:153–176 (1991)). As mentioned above, only serpins had been known to be able to bind and inhibit t-PA. When the structure of an inhibitor from E. caffra was crystallographically determined (Onesti, S. et al., *J. Molec. Biol.* 217:153–176 (1991)), it showed a P1 loop with the same canonical form as Kunitz and Kazal inhibitors for the backbone and Cβ carbons. The entire loop itself was more exposed from the surface, and more flexible, as estimated from B-values, than the loops in Kazal inhibitors. Also, the overall width of the P1 loop in the E. caffra inhibitor, as measured from P4 to P3' Cα is 3 to 6.5 Å narrower than in Kunitz and Kazal inhibitors (Onesti, S. et al., *J. Molec. Biol.* 217:153–176 (1991)). Increasing flexibility between the P3 and P6' cystines might enable the Kazal derived inhibitors to bind plasminogen activators better than they currently do.

EXAMPLE 6

Contact Determinants

The inhibitory capacity of the molecules of the present invention may result either from the introduction of residues in the OM3TKY that make better contacts with UK than the wild type OM3TKY does, or the removal of residues that formed bad contacts between wild type OM3TKY and UK. The fact that the P1 change to arginine did not increase affinity indicates that other residues, besides the residue at P1, are also determinants of binding. The presence of a bulky β-branched residue, Ile at P1' and an aromatic Tyr, at P2' in PSTI would indicate that the size of these residues and simple steric contacts between these residues and urokinase are not a major determinant of specificity. The nature of the contacts, such as possible charge interactions and hydrogen bonds, may be the determining factors.

Also of interest is a report of the basis of trypsin-like serine protease specificity for natural substrates (Hedstrom, L. et al., *Science* 255:1249–1253 (1992)). This report suggested that while the S1 residue of a substrate contains the specificity for the cleavage site, other sections of the protease, outside the active site pocket, help to determine which proteins are chosen as substrates. These sections are residues 184–189 and 221–225 of chymotrypsin and represent loops that border the sequences that make up the chymotrypsin hydrophobic binding pocket (Hedstrom, L. et al., *Science* 255:1249–1253 (1992)). In the modelling of the present invention, these residues did not appear to come into proximity with either BPTI or OM3TKY inhibitors.

EXAMPLE 7

Ligand Searching by Phage Display

Further mutations and refinements to the above-described mutants can be accomplished by creating a library of inhibitors that bind UK, and which would therefore aid in identifying the permissible contact residues.

In order to generate a library of inhibitors with affinity, and possibly specificity, for UK more rapidly, the method of protein ligand screening known as a phage display system can be employed. In general, this method involves expressing a fusion protein in which the desired protein ligand is fused to the C-terminal domains of the M13 Gene III coat protein (Lowman, H. B. et al., *Biochem.* 30:10832–10838 (1991); Markland, W. et al., *Gene* 109:13–19 (1991); Roberts, B. L. et al., *Proc. Natl. Acad. Sci.* (*U.S.A.*)

89:2429–2433 (1992); Smith, G. P., *Science* 228:1315–1317 (1985); Smith, R. P. et al., *Science* 248:1126–1128 (1990), all herein incorporated by reference). A fusion of the Pancreatic Secretory Trypsin Inhibitor (PSTI) to the C-terminal domain of M13 Gene III can be made. Expression of mutants of this fusion coat protein on the surface of M13 phages results in phages that can be passed through a urokinase affinity column, and allows for purification of the DNA packaged within the phages. This DNA will code for the mutants with affinity for UK, and can subsequently be amplified and sequenced.

In one embodiment, a plasmid, to be called pTACZZG3, can be constructed which has tetracycline and ampicillin resistance, fl origin, the tac inducible promoter, the signal sequence and two protein A domains from pEZZ318, and the C-terminal portion of M13 Gene III. This fragment should contain the M13 Gene III region coding from residue 197 of the Gene III product to the AluI site at nucleotide position 2964 (GCG numbering) of M13.

An insert coding for PSTI is constructed from four synthetic oligonucleotides (Table 4) and ligated into pTAC-ZZG3 between the EcoRI and SstI sites. This will direct the synthetic PSTI gene into the proper orientation, and allow for proper peptide linker regions to be in the expressed polypeptide, and the insertion of an amber stop codon following the coding sequences of the PSTI gene. This synthetic gene sequence has three unique restriction sites, which aid in the insertion of randomized DNA cassettes at the intended sites of mutagenesis in the inhibitor.

Cassette mutagenesis is thus conducted on this construct by methods analogous to those described by Lowman, H. B. (*Biochem.* 30:10832–10838 (1991)). Screening of PSTI variants is done by M13K07 assisted growth of phage with the PSTI-Gene III fusion expressed on the phage surface (Lowman, H. B. et al., *Biochem.* 30:10832–10838 (1991)). These altered phages are bound to urokinase attached to a solid phase (for example, beads) to select for PSTI variants on the phage with increased affinity to UK. These selected phage can be grown and sequenced, and also alternatively expressed in a non-amber suppressor strain to obtain a Protein A/PSTI fusion protein without the C-terminal portion of Gene III expressed (Lowman, H. B. et al., *Biochem.* 30:10832–10838 (1991)). Other methods of combinatorial library screening, which will be apparent to those skilled in the art, can also be used to isolate PSTI-like or other Kazal-type inhibitors having increased affinity to urokinase. For example, the a synthetic approach to combinatorial cassette nutagenesis (or "CCM") may be used (Hermes, J. D. et al., *Proc. Natl. Acad. Sci. (U.S.A.)* 87:696–700 (1990); Lim, W. A. et al. *Nature* 339:31–36 (1989); Reidhaarolson, J. F. et al., *Science* 241:53– 57 (1988); Oliphant, A. R., et al., *Gene* 44:177–183 (1986), all herein incorporated by reference). Alternatively, methods of random mutagenesis (Leatherbarrow, R. *J. Prot. Eng.* 1:7–16 (1986); Knowles, J. R., *Science* 236:1252–1258 (1987); Shaw, W. V., *Biochem. J.* 246:1–17 (1987); Gerit, J. A. *Chem. Rev.* 87:1079–1105 (1987)) or site-directed mutagenesis (Craik, C. S., *Science* 228:291–297 (1985); Cronin, C. S. et al., *Biochem.* 27:4572–4579 (1988); Wilks, H. M. et al., *Science* 242:1541–1544 (1988))) may be employed in order to produce the desired variant proteins and polypeptide mimetics.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

---

What is claimed is:

1. A low molecular weight proteinaceous inhibitor of urokinase, wherein said inhibitor is selected from the group consisting of:

(A) an inhibitor comprising an amino acid sequence of:
Val-Asp-Cys-Ser-Glu-Tyr-Pro-Lys-Pro-Ala-Cys-Gly-Arg-Thr-Gly-His-Pro-Leu-Cys-Gly-Ser-Asp-Asn-Lys-Thr-Tyr-Gly-Asn-Lys-Cys-Asn-Phe-Cys-Asn-Ala-Val -Val-Flu-Ser-Asn-Gly-Thr-Leu-Thr-Leu-Ser-His-Phe-Gly-Lys-Cys (SEQ ID NO:7);

(B) an inhibitor comprising an amino acid sequence of:
Val-Asp-Cys-Ser-Glu-Tyr-Pro-Lys-Pro-Ala-Cys-Ala-Arg-Met-Ala   -Ala-Pro-Leu-Cys-Gly-Ser-Asp-Asn-Lys-Thr-Tyr-Gly-Asn-Lys-Cys   -Asn-Phe-Cys-Asn-Ala-Val-Val-Glu-Ser-Asn-Gly-Thr-Leu-Thr-Leu -Ser-His-Phe-Gly-Lys-Cys (SEQ ID NO:8);

(C) an inhibitor comprising an amino acid sequence of:
Val-Asp-Cys-Ser-Glu-Tyr-Pro-Lys-Pro-Ala-Cys-Gly-Arg-Val-Val -Gly-Pro-Leu-Cys-Gly-Ser-Asp-Asn-Lys-Thr-Tyr-Gly-Asn-Lys-Cys   -Asn-Phe-Cys-Asn-Ala-Val-Val-Glu-Ser-Asn-Gly-Thr-Leu-Thr-Leu -Ser-His-Phe-Gly-Lys-Cys (SEQ ID NO:9); and (D) an inhibitor comprising an amino acid sequence of:
Val-Asp-Cys-Ser-Glu-Tyr-Pro-Lys-Pro-Ala-Cys-Ala-Arg-Ser-Ser -Ala-Pro-Leu-Cys-Gly-Ser-Asp-Asn-Lys-Thr-Tyr-Gly-Asn-Lys-Cys   -Asn-Phe-Cys-Asn-Ala-Val-Val-Glu-Ser-Asn-Gly-Thr-Leu-Thr-Leu -Ser-His-Phe-Gly-Lys-Cys (SEQ ID NO:10).

2. The inhibitor of claim 1 that comprises an amino acid sequence of (SEQ ID NO:7):
Val-Asp-Cys-Ser-Glu-Tyr-Pro-Lys-Pro-Ala-Cys-Gly-Arg-Thr-Gly   -His-Pro-Leu-Cys-Gly-Ser-Asp-Asn-Lys-Thr-Tyr-Gly-Asn-Lys-Cys   -Asn-Phe-Cys-Asn-Ala-Val-Val-Glu-Ser-Asn-Gly-Thr-Leu-Thr-Leu -Ser-His-Phe-Gly-Lys-Cys.

3. The inhibitor of claim 1 that comprises an amino acid sequence of (SEQ ID NO:8):
Val-Asp-Cys-Ser-Glu-Tyr-Pro-Lys-Pro-Ala-Cys-Ala-Arg-Met-Ala   -Ala-Pro-Leu-Cys-Gly-Ser-Asp-Asn-Lys-Thr-Tyr-Gly-Asn-Lys-Cys   -Asn-Phe-Cys-Asn-Ala-Val-Val-Glu-Ser-Asn-Gly-Thr-Leu-Thr-Leu -Ser-His-Phe-Gly-Lys-Cys.

4. The inhibitor of claim 1 that comprises an amino acid sequence of (SEQ ID NO:9):
Val-Asp-Cys-Ser-Glu-Tyr-Pro-Lys-Pro-Ala-Cys-Gly-Arg-Val-Val -Gly-Pro-Leu-Cys-Gly-Ser-Asp-Asn-Lys-Thr-Tyr-Gly-Asn-Lys-Cys   -Asn-Phe-Cys-Asn-Ala-Val-Val-Glu-Ser-Asn-Gly-Thr-Leu-Thr-Leu -Ser-His-Phe-Gly-Lys-Cys.

5. The inhibitor of claim 1 that comprises an amino acid sequence of (SEQ ID NO:10):
Val-Asp-Cys-Ser-Glu-Tyr-Pro-Lys-Pro-Ala-Cys-Ala-Arg-Ser-Ser -Ala-Pro-Leu-Cys-Gly-Ser-Asp-Asn-Lys-Thr-Tyr-Gly-Asn-Lys-Cys   -Asn-Phe-Cys-Asn-Ala-Val-Val-Glu-Ser-Asn-Gly-Thr-Leu-Thr-Leu -Ser-His-Phe-Gly-Lys-Cys.

6. The inhibitor of claim 1, wherein said inhibitor is joined to another moiety.

7. The inhibitor of claim 6, wherein said moiety is a protein or a domain of a protein.

8. The inhibitor of claim 6, wherein said joining is accomplished by conjugating said inhibitor to said moiety.

9. The inhibitor of claim 8, wherein said moiety is a protein or a domain of a protein.

10. The inhibitor of claim 7, wherein said joining is accomplished by forming a fusion protein containing said inhibitor and said one or more domains of a protein.

11. The inhibitor of claim 7, wherein said moiety comprises an antigen binding domain of an antibody.

12. The inhibitor of claim 7, wherein said moiety comprises a receptor ligand.

13. The inhibitor of claim 7, wherein said receptor ligand is a urokinase receptor ligand.

14. The inhibitor of claim 7, wherein said moiety comprises a ligand binding protein, or a domain thereof.

15. A low molecular weight proteinaceous inhibitor of urokinase, wherein said inhibitor is produced by a process comprising the steps:

(A) identifying a set of amino acid residues in a proteinaceous urokinase substrate that correspond to a set of amino acid residues in a Kazal-type protease inhibitor by aligning:

(I) the amino acid sequence of said proteinaceous urokinase substrate, said amino acid sequence (I) comprising a scissile bond-containing region of said substrate, with

(11) the amino acid sequence of the P1 loop of a Kazal-type protease inhibitor, said amino acid sequence (11) comprising a P1 loop, and having P2–P3' residues; such that the scissile bond of said substrate is aligned with the P1-P1' bond of said protease inhibitor; wherein said aligned amino acid sequences of (I) and (11) define said set of corresponding amino acid residues; and (B) synthesizing a proteinacous molecule wherein said P2–P3' residues of said inhibitor have been replaced by the corresponding residues of said substrate wherein said low molecular weight proteinaceous inhibitor of urokinase comprises a polypeptide having an amino acid sequence selected from the group consisting of SEQ ID NO:7, SEQ ID NO:8, SEQ ID NO:9, and SEQ ID NO:10.

16. A low molecular weight proteinaceous inhibitor of urokinase, wherein said inhibitor is produced by synthesizing a proteinacous molecule having the amino acid sequence of a Kazal-type protease inhibitor, said inhibitor having a P1 loop, and having P2–P3' residues, wherein said P2–P3' amino acid residues of said inhibitor are amino acid residues of a proteinaceous urokinase substrate that correspond to said P2–P3' amino acid residues when:

(I) the amino acid sequence of said proteinaceous urokinase substrate, said amino acid sequence (I) comprising a scissile bond-containing region of said substrate, is aligned with (II) the amino acid sequence of the P1 loop of said Kazal-type protease inhibitor, said amino acid sequence (II) comprising a P1 loop, and having P2–P3' residues;

such that the scissile bond of said substrate is aligned with the P1–P1' bond of said protease inhibitor.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 184 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v i i ) IMMEDIATE SOURCE:
        ( B ) CLONE: STAPHYLOCCOCAL PROTEIN A - TURKEY OVOMUCOID DOMAIN FUSION ( x i ) SEQUENCE DESCRIPTION: SEQ ID NO:1:

```
Ala  Ala  Gln  His  Asp  Glu  Ala  Val  Asp  Asn  Lys  Phe  Asn  Lys  Glu  Gln
 1              5                        10                      15

Gln  Asn  Ala  Phe  Tyr  Glu  Ile  Leu  His  Leu  Pro  Asn  Leu  Asn  Glu  Glu
              20                        25                      30

Gln  Arg  Asn  Ala  Phe  Ile  Gln  Ser  Leu  Lys  Asp  Asp  Pro  Ser  Gln  Ser
```

|   |   |   |   |   | 35 |   |   |   |   | 40 |   |   |   |   | 45 |   |   |   |
|---|---|---|---|---|---|---|---|---|---|---|---|---|---|---|---|---|---|---|

Ala Asn Leu Leu Ala Glu Ala Lys Lys Leu Asn Asp Ala Gln Ala Pro
    50                        55                    60

Lys Val Asp Asn Lys Phe Asn Lys Glu Gln Gln Asn Ala Phe Tyr Glu
65                    70                    75                  80

Ile Leu His Leu Pro Asn Leu Asn Glu Glu Gln Arg Asn Ala Phe Ile
                  85                    90                  95

Gln Ser Leu Lys Asp Asp Pro Ser Gln Ser Ala Asn Leu Leu Ala Glu
            100                 105                110

Ala Lys Lys Leu Asn Asp Ala Gln Ala Pro Lys Val Asp Arg Lys Glu
        115                  120              125

Ala His Phe Ala Met Val Asp Cys Ser Glu Tyr Pro Lys Pro Ala Cys
    130                  135                140

Thr Leu Glu Tyr Arg Pro Leu Cys Gly Ser Asp Asn Lys Thr Tyr Gly
145                  150                155              160

Asn Lys Cys Asn Phe Cys Asn Ala Val Val Glu Ser Asn Gly Thr Leu
              165                170              175

Thr Leu Ser His Phe Gly Lys Cys
            180

( 2 ) INFORMATION FOR SEQ ID NO:2:

( i ) SEQUENCE CHARACTERISTICS:
        ( A ) LENGTH: 51 amino acids
        ( B ) TYPE: amino acid
        ( D ) TOPOLOGY: linear ( i i ) MOLECULE TYPE: protein ( i i i ) HYPOTHETICAL: NO ( v i i ) IMMEDIATE SOURCE:
        ( B ) CLONE: TURKEY OVOMUCOID DOMAIN 3

( x i ) SEQUENCE DESCRIPTION: SEQ ID NO:2:

Val Asp Cys Ser Glu Tyr Pro Lys Pro Ala Cys Thr Leu Glu Tyr Arg
1                  5                    10                  15

Pro Leu Cys Gly Ser Asp Asn Lys Thr Tyr Gly Asn Lys Cys Asn Phe
            20                    25                  30

Cys Asn Ala Val Val Glu Ser Asn Gly Thr Leu Thr Leu Ser His Phe
        35                  40                  45

Gly Lys Cys
       50

( 2 ) INFORMATION FOR SEQ ID NO:3:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: YES ( i v ) ANTI-SENSE: NO ( v i i ) IMMEDIATE SOURCE:
        ( B ) CLONE: 88 OLIGONUCLEOTIDE ( x i ) SEQUENCE DESCRIPTION: SEQ ID NO:3:

GTTGTCGGAG CCACAGAGAG GATGTCCCGT TCGTCCGCAT GCAGG        45

( 2 ) INFORMATION FOR SEQ ID NO:4:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: YES ( i v ) ANTI-SENSE: NO ( v i i ) IMMEDIATE SOURCE:
        ( B ) CLONE: 89 OLIGONUCLEOTIDE ( x i ) SEQUENCE DESCRIPTION: SEQ ID NO:4:

GTTGTCGGAG CCACAGAGAG GTGCTGCCAT TCGTGCGCAT GCAGG    45

( 2 ) INFORMATION FOR SEQ ID NO:5:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: YES ( i v ) ANTI-SENSE: NO ( v i i ) IMMEDIATE SOURCE:
        ( B ) CLONE: 90 OLIGONUCLEOTIDE ( x i ) SEQUENCE DESCRIPTION: SEQ ID NO:5:

GTTGTCGGAG CCACAGAGAG GTCCAACAAC TCGTCCGCAT GCAGG    45

( 2 ) INFORMATION FOR SEQ ID NO:6:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: YES ( i v ) ANTI-SENSE: NO ( v i i ) IMMEDIATE SOURCE:
        ( B ) CLONE: 91 OLIGONUCLEOTIDE ( x i ) SEQUENCE DESCRIPTION: SEQ ID NO:6:

GTTGTCGGAG CCACAGAGAG GTGCGGAGGA TCGTGCGCAT GCAGG    45

( 2 ) INFORMATION FOR SEQ ID NO:7:

( i ) SEQUENCE CHARACTERISTICS:
        ( A ) LENGTH: 51 amino acids
        ( B ) TYPE: amino acid
        ( D ) TOPOLOGY: linear ( i i ) MOLECULE TYPE: protein ( i i i ) HYPOTHETICAL: YES ( v i i ) IMMEDIATE SOURCE:
        ( B ) CLONE: OM3TKY clone 88 inhibitor ( x i ) SEQUENCE DESCRIPTION: SEQ ID NO:7:

```
Val  Asp  Cys  Ser  Glu  Tyr  Pro  Lys  Pro  Ala  Cys  Gly  Arg  Thr  Gly  His
1              5                        10                       15

Pro  Leu  Cys  Gly  Ser  Asp  Asn  Lys  Thr  Tyr  Gly  Asn  Lys  Cys  Asn  Phe
               20                       25                       30

Cys  Asn  Ala  Val  Val  Glu  Ser  Asn  Gly  Thr  Leu  Thr  Leu  Ser  His  Phe
          35                       40                       45

Gly  Lys  Cys
          50
```

( 2 ) INFORMATION FOR SEQ ID NO:8:

( i ) SEQUENCE CHARACTERISTICS:
        ( A ) LENGTH: 51 amino acids
        ( B ) TYPE: amino acid
        ( D ) TOPOLOGY: linear ( i i ) MOLECULE TYPE: protein ( i i i ) HYPOTHETICAL: YES ( v i i ) IMMEDIATE SOURCE:
        ( B ) CLONE: OM3TKY clone 89 inhibitor ( x i ) SEQUENCE DESCRIPTION: SEQ ID NO:8:

```
Val  Asp  Cys  Ser  Glu  Tyr  Pro  Lys  Pro  Ala  Cys  Ala  Arg  Met  Ala  Ala
1              5                        10                       15

Pro  Leu  Cys  Gly  Ser  Asp  Asn  Lys  Thr  Tyr  Gly  Asn  Lys  Cys  Asn  Phe
               20                       25                       30

Cys  Asn  Ala  Val  Val  Glu  Ser  Asn  Gly  Thr  Leu  Thr  Leu  Ser  His  Phe
          35                       40                       45

Gly  Lys  Cys
          50
```

( 2 ) INFORMATION FOR SEQ ID NO:9:

( i ) SEQUENCE CHARACTERISTICS:
        ( A ) LENGTH: 51 amino acids
        ( B ) TYPE: amino acid
        ( D ) TOPOLOGY: linear ( i i ) MOLECULE TYPE: protein ( i i i ) HYPOTHETICAL: YES ( v i i ) IMMEDIATE SOURCE:
        ( B ) CLONE: OM3TKY clone 90 inhibitor ( x i ) SEQUENCE DESCRIPTION: SEQ ID NO:9:

```
Val  Asp  Cys  Ser  Glu  Tyr  Pro  Lys  Pro  Ala  Cys  Gly  Arg  Val  Val  Gly
1              5                        10                       15

Pro  Leu  Cys  Gly  Ser  Asp  Asn  Lys  Thr  Tyr  Gly  Asn  Lys  Cys  Asn  Phe
               20                       25                       30

Cys  Asn  Ala  Val  Val  Glu  Ser  Asn  Gly  Thr  Leu  Thr  Leu  Ser  His  Phe
          35                       40                       45

Gly  Lys  Cys
          50
```

( 2 ) INFORMATION FOR SEQ ID NO:10:

( i ) SEQUENCE CHARACTERISTICS:
        ( A ) LENGTH: 51 amino acids
        ( B ) TYPE: amino acid
        ( D ) TOPOLOGY: linear ( i i ) MOLECULE TYPE: protein ( i i i ) HYPOTHETICAL: YES ( v i i ) IMMEDIATE SOURCE:
    ( B ) CLONE: OM3TKY clone 91 inhibitor ( x i ) SEQUENCE DESCRIPTION: SEQ ID NO:10:

| Val | Asp | Cys | Ser | Glu | Tyr | Pro | Lys | Pro | Ala | Cys | Ala | Arg | Ser | Ser | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Pro | Leu | Cys | Gly | Ser | Asp | Asn | Lys | Thr | Tyr | Gly | Asn | Lys | Cys | Asn | Phe |
|     |     |     | 20  |     |     |     |     | 25  |     |     |     |     | 30  |     |     |
| Cys | Asn | Ala | Val | Val | Glu | Ser | Asn | Gly | Thr | Leu | Thr | Leu | Ser | His | Phe |
|     |     | 35  |     |     |     |     | 40  |     |     |     |     | 45  |     |     |     |
| Gly | Lys | Cys |     |     |     |     |     |     |     |     |     |     |     |     |     |
|     | 50  |     |     |     |     |     |     |     |     |     |     |     |     |     |     |